(12) United States Patent
Mitragotri et al.

(10) Patent No.: US 9,814,422 B2
(45) Date of Patent: *Nov. 14, 2017

(54) COMPOSITIONS FOR SOLUBILIZING CELLS AND/OR TISSUE

(75) Inventors: Samir Mitragotri, Santa Barbara, CA (US); Byeong Hee Hwang, Goleta, CA (US); Nishit Doshi, Mountain View, CA (US); Kenneth Tsai, Houston, TX (US); Russell Lebovitz, San Diego, CA (US)

(73) Assignees: THE REGENTS OF THE UNIVERSITY OF CALIFORNIA, Oakland, CA (US); DX BIOSCIENCES, INC., San Diego, CA (US)

(*) Notice: Subject to any disclaimer, the term of this patent is extended or adjusted under 35 U.S.C. 154(b) by 752 days.

This patent is subject to a terminal disclaimer.

(21) Appl. No.: 13/432,978

(22) Filed: Mar. 28, 2012

(65) Prior Publication Data

US 2015/0275174 A1 Oct. 1, 2015

Related U.S. Application Data

(63) Continuation-in-part of application No. 13/095,639, filed on Apr. 27, 2011, now Pat. No. 8,389,582, which is a continuation-in-part of application No. 12/664,994, filed as application No. PCT/US2008/072384 on Aug. 6, 2008, said application No. 13/095,639 is a continuation-in-part of application No. 13/126,105, filed as application No. PCT/US2010/024010 on Feb. 12, 2010, now Pat. No. 8,945,482.

(60) Provisional application No. 60/963,773, filed on Aug. 6, 2007, provisional application No. 61/152,585, filed on Feb. 13, 2009.

(51) Int. Cl.

| | | |
|---|---|---|
| A61B 5/00 | (2006.01) |
| C07K 1/14 | (2006.01) |
| A61K 9/06 | (2006.01) |
| A61K 31/205 | (2006.01) |
| A61K 31/765 | (2006.01) |
| A61K 9/00 | (2006.01) |
| C07K 16/18 | (2006.01) |
| C12N 1/06 | (2006.01) |

(52) U.S. Cl.
CPC ............ *A61B 5/443* (2013.01); *A61K 9/0014* (2013.01); *A61K 9/06* (2013.01); *A61K 31/205* (2013.01); *A61K 31/765* (2013.01); *C07K 1/14* (2013.01); *A61K 9/0009* (2013.01); *C07K 16/18* (2013.01); *C07K 2317/52* (2013.01); *C07K 2317/94* (2013.01); *C12N 1/06* (2013.01)

(58) Field of Classification Search
None
See application file for complete search history.

(56) References Cited

U.S. PATENT DOCUMENTS

| | | |
|---|---|---|
| 3,962,150 A | 6/1976 | Viola |
| 4,214,908 A | 7/1980 | Deguchi et al. |
| 4,268,613 A | 5/1981 | Okishi |
| 5,398,690 A | 3/1995 | Batten et al. |
| 5,492,126 A | 2/1996 | Hennige et al. |
| 5,639,630 A | 6/1997 | Malin et al. |
| 5,696,069 A | 12/1997 | Ito et al. |
| 5,739,432 A | 4/1998 | Sinha |
| 5,804,452 A | 9/1998 | Pronovost et al. |
| 5,913,833 A | 6/1999 | Elstrom et al. |
| 6,007,497 A | 12/1999 | Huitema |
| 6,093,551 A | 7/2000 | Raithel et al. |
| 6,165,500 A | 12/2000 | Cevic |
| 6,190,315 B1 * | 2/2001 | Kost ................ A61M 37/0092 600/309 |
| 6,328,728 B1 | 12/2001 | Holladay et al. |
| 6,544,211 B1 | 4/2003 | Andrew et al. |
| 6,560,478 B1 | 5/2003 | Alfano et al. |
| 6,589,173 B1 | 7/2003 | Mitragotri |
| 7,608,278 B2 | 10/2009 | Hoiseth et al. |
| 7,709,193 B2 | 5/2010 | Van Eyk et al. |

(Continued)

FOREIGN PATENT DOCUMENTS

| | | |
|---|---|---|
| CN | 102395881 A | 3/2012 |
| EP | 0743519 A2 | 11/1996 |
| JP | 2001502693 A | 2/2001 |
| JP | 2005336241 A | 12/2005 |
| JP | 2006167428 A | 6/2006 |
| JP | 2010115132 A | 5/2010 |
| WO | 2005009510 A2 | 2/2005 |
| WO | 2006026248 A1 | 3/2006 |
| WO | 2010093861 A2 | 8/2010 |

OTHER PUBLICATIONS

Tasseron, JG et al. Partial purification of soluble protein from mouse skin to which carcinogenic hydrocarbons are specifically bound. Biochemistry. 1970. 9(7): 1636-1644.*
3-(N,N-Dimethylmyristylammonio)propanesulfonate. Product sheets [online]. Sigma-Aldrich, 2016 [retrieved on Jun. 23, 2016]. Retrieved from the Internet: <URL: http://www.sigmaaldrich.com/catalog/product/sigma/t7763?lang=en&region=US>.*

(Continued)

*Primary Examiner* — Renee Claytor
*Assistant Examiner* — Susan E Fernandez
(74) *Attorney, Agent, or Firm* — Benesch Friedlander Coplan & Aronoff LLP

(57) ABSTRACT

Solubilizing compositions are provided that include a 3-(alkyl dimethyl ammonia) propane sulfonate zwitterionic surfactant and a polyethylene glycol alkyl ether nonionic surfactant, provided that the zwitterionic surfactant and the nonionic surfactant are not simultaneously and respectively 3-(decyl dimethyl ammonia) propane sulfonate and polyoxyethylene (4) lauryl ether. Also provided are methods for solubilizing cells and/or tissue of a subject in vivo and methods for recovering proteins from skin cells of a subject in vivo using the solubilizing compositions.

16 Claims, 19 Drawing Sheets

(56) References Cited

U.S. PATENT DOCUMENTS

| | | | |
|---|---|---|---|
| 8,389,582 B2* | 3/2013 | Mitragotri | A61K 9/0009 514/642 |
| 8,642,664 B2* | 2/2014 | Mitragotri et al. | 514/723 |
| 2002/0082518 A1 | 6/2002 | Weiss et al. | |
| 2002/0188280 A1 | 12/2002 | Nguyen et al. | |
| 2003/0060818 A1 | 3/2003 | Kannenberg et al. | |
| 2003/0143116 A1 | 7/2003 | Zheng et al. | |
| 2003/0211520 A1 | 11/2003 | Afar et al. | |
| 2004/0151745 A1 | 8/2004 | Zimmer et al. | |
| 2004/0191854 A1 | 9/2004 | Lapen et al. | |
| 2005/0164903 A1 | 7/2005 | Ko et al. | |
| 2005/0214825 A1 | 9/2005 | Stuelpnagel | |
| 2006/0046261 A1 | 3/2006 | Porter et al. | |
| 2006/0100569 A1 | 5/2006 | McRury et al. | |
| 2006/0116563 A1 | 6/2006 | Asano et al. | |
| 2006/0165823 A1 | 7/2006 | Herrera | |
| 2006/0166222 A1 | 7/2006 | Lu et al. | |
| 2007/0055181 A1 | 3/2007 | Deem et al. | |
| 2007/0055261 A1 | 3/2007 | Reiley et al. | |
| 2007/0059268 A1 | 3/2007 | Magee | |
| 2007/0059687 A1 | 3/2007 | Ohno et al. | |
| 2007/0173448 A1 | 7/2007 | Shah et al. | |
| 2007/0183936 A1 | 8/2007 | Newsam et al. | |
| 2008/0003575 A1* | 1/2008 | Michalik | C12N 15/1003 435/6.12 |
| 2008/0039340 A1* | 2/2008 | Kornblau et al. | 506/12 |
| 2008/0200545 A1 | 8/2008 | Aubrum-Sonneville et al. | |
| 2009/0269380 A1 | 10/2009 | Baker, Jr. et al. | |
| 2009/0304799 A1 | 12/2009 | Baker, Jr. et al. | |
| 2009/0325837 A1 | 12/2009 | Mundschau et al. | |
| 2010/0120171 A1* | 5/2010 | Vilgrain et al. | 436/501 |
| 2010/0226983 A1 | 9/2010 | Sutcliffe et al. | |
| 2010/0261176 A1 | 10/2010 | Mitragotri et al. | |
| 2011/0212485 A1 | 9/2011 | Mitragotri et al. | |
| 2011/0262892 A1 | 10/2011 | Aoyagi et al. | |
| 2011/0295149 A1 | 12/2011 | Mitragotri et al. | |
| 2012/0004592 A1 | 1/2012 | Mitragotri et al. | |
| 2012/0064136 A1 | 3/2012 | Baker, Jr. et al. | |
| 2012/0253238 A1 | 10/2012 | Mitragotri et al. | |
| 2014/0107560 A1 | 4/2014 | Mitragotri et al. | |
| 2015/0344834 A1 | 12/2015 | Mitragotri et al. | |

OTHER PUBLICATIONS 3-(Decyldimethylammonio)propanesulfonate inner salt. Product sheets [online]. Sigma-Aldrich, 2016 [retrieved on Jun. 23, 2016]. Retrieved from the Internet: <URL: http://www.sigmaaldrich.com/catalog/product/sigma/d4266?lang=en&region=US>.*

Brij 35. Product sheets [online]. Sigma-Aldrich, 2016 [retrieved on Jun. 23, 2016]. Retrieved from the Internet: <URL: http://www.sigmaaldrich.com/catalog/product/aldrich/858366?lang=en&region=US>.*

Tutulan-Cunita et al., "Mutational analysis of the yeast multidrug resistance ABC transporter Pdr5p with altered drug specificity", Genes to cells (2005) vol. 10, pp. 409-420.

Pubchem polidocanol (pubchem.ncbi.nlm.nih.gov/summary/summary.cgi?cid=24750&loc=ec_rcs, downloaded Oct. 29, 2012.

Huang et al., "Separation and measurement of desmosine and isodesmosine in vascular tissue hydrolysates by micellar electrokinetic capillary chromatography with a mixed micelle system", J. Chromaography A 1175 : 294-296 (2007), Abstract only.

Written Opinion and International Search Report of the International Searching Authority from related PCT Application No. PCT/US08/72384, dated Jun. 9, 2009.

Ayliffe, et al. "Hand disinfection: a comparison of various agents in laboratory and ward studies" J. Hospital Infection, 1988, 11, 226-243.

Sakai, et al. "Contribution of Calcium Ion Sequestration by Polyoxyethylated Nonionic Surfactants to the Enhanced Colonic Absorption of p-Aminobenzoic Acid"' J. Pharm. Sci. 1986, 75, 387-390.

Prasanthi and Lakshmi, "Effect of Chemical Enhancers in Transdermal Permeation of Alfuzosin Hydrochloride" ISRN Pharm. 2012, 1-8.

Malminen, et al. "Functional Expression of NFI Tumor Suppressor Protein: Association with Keratin Intermediate Filaments During the Early Development of Human Epidermis" BMC Derm. 2002, 2, 1471-5945.

Harmon Stores Product Sheet, Calamine Lotion: www.harmondiscount.com, Published online Feb. 1, 2001.

Guenthner, "Gram-Negative Bacilli as Nontransient Flora on the Hands of Hospital Personnel" J. Clin, Microbio. 1986, 25, 488-490.

Sugimura, et al., "Transgenic Patchouli Plants Produced by Agrobacteriurn-mediated Transformation" Plant Cell, Tissue, Organ Culture 2005, 82, 251-257.

Zanten, et al., "Cerebrospinal Fluid Tumour Markers in Patient Treated for Meningeal Malignancy" JNNP 1991, 54, 119-123.

Huang, et al., "Separation and Measurement of Desmosine and Isodesmosine in Vascular Tissue Hydrolysates by Micellar Electrokinetic Capillary Chromatography with a Mixed Micelle System" J. Chromatography A 2007, 1175, 294-296.

Detergent Selection Table, accessed Jun. 20, 2016: http://www.science.co.il/Biomedical/detergent_selection_table.pdf.

Buffers and Stock Solutions, accessed Jun. 21, 2016: http://www.abcam.com/ps/pdf/protocols/buffers%20and%20stock%20solutions.pdf.

Bakshi and Kaur, "Mixed Micelle Behavior of Poly(ethylene glycol) alkyl ethers with Series of Monomeric Cationic, Phosphonium Cationic, and Zwitterionic Surfactant" Colloid Polym. Sci. 2006, 285, 101-106.

European Search Opinion in related application European Pat App. No. 12876815.7, dated Sep. 12, 2016.

Paliwal, et al., "One-Step Acquisition of Functional Biomolecules from Tissues" PNAS 2010, 107, 14627-14632.

European Search Report and Opinion in related European Pat. App. No. 16161790.7, dated Aug. 31, 2016.

European Search Report and Opinion in related European Pat. App. No. 16154949.8, dated Aug. 25, 2016.

Williams, et al., "Endoscopic ultrasound guided fine needle aspiration biopsy: a large single centre experience," Gut 1999, 44, 720-726.

* cited by examiner

COMPOSITIONS FOR SOLUBILIZING CELLS AND/OR TISSUE

CROSS-REFERENCE TO RELATED APPLICATIONS

This application is a continuation-in-part application of U.S. patent application Ser. No. 13/095,639, filed on Apr. 27, 2011. U.S. patent application Ser. No. 13/095,639 is a continuation-in-part application of U.S. patent application Ser. No. 12/664,994, filed on Jun. 29, 2010 as a U.S. National Stage filing of PCT/US2008/072384, filed on Aug. 6, 2008, which, in turn, claims priority to U.S. Provisional Patent Application Ser. No. 60/963,773, filed on Aug. 6, 2007. U.S. patent application Ser. No. 13/095,639 is also a continuation-in-part application of Ser. No. 13/126,105, filed on Apr. 26, 2011 as a U.S. National Stage filing of PCT/US2010/024010, filed on Feb. 12, 2010, which, in turn, claims priority to U.S. Provisional Patent Application Ser. No. 61/152,585, filed on Feb. 13, 2009. All of these related applications are incorporated by reference herein in their entireties.

STATEMENT REGARDING FEDERALLY SPONSORED RESEARCH OR DEVELOPMENT

This invention was made with government support under federal grant number W81XWH-06-01-00400 awarded by the United States Army. The United States Government has certain rights in this invention.

BACKGROUND

Skin is the "window" to the body. Skin is unique among the body's organs for several reasons: (1) skin is the largest organ of the human body; (2) skin is directly exposed to the environment; (3) skin is an excellent excretory organ; (4) skin is the most visible and accessible organ of the body; and (5) skin is a highly active immune organ of the body.

Skin has another important quality: The molecular profile of skin has information that is valuable for physiological monitoring of, among other things, small organic molecules, proteins, DNA, RNA, and lipids. Much can be learned from skin's molecular profiling. For example, pathogens (e.g., bacteria) that grow on skin may allow for forensic identification. Skin's molecular profile may reveal environmental factors to which the body has been passively exposed. These environmental factors may range from the mundane, e.g., allergens, toxins, and cosmetic products, to the industrial and/or agricultural, e.g., industrial solvents, fertilizers, and pesticides, to the dangerous, e.g., explosives and other warfare agents.

Skin's molecular profile may also reveal factors to which the body has been actively exposed. More particularly, skin's molecular profile may reveal what the body has consumed. For example, abused substances (e.g., illegal drugs or narcotics) and therapeutic drugs (e.g., tramadol, fluconazole, barbitals, and anabolic steroids) may be found in skin for weeks after consumption.

Skin's molecular profile may also aid in the diagnosis of conditions and diseases. For example, skin cholesterol is a proxy of the extent of arterial blocks. Glycation of skin collagen is an indicator of a history of diabetes. Skin deposition of β-amyloids may indicate the existence and extent of Alzheimer's disease. And skin globular proteins (e.g., IgE) may indicate allergies to specific allergens.

Several methods exist for sampling biomolecules from skin. For example, one current method is skin biopsy. However, skin biopsy is invasive and analysis is difficult. Practically speaking, skin biopsy is designed for well-equipped experts and, thus, its use in a point-of-care setting is limited. Another current method for sampling biomolecules from skin, tape stripping, suffers from these same limitations and is generally unacceptable because of variability in results. Yet another current method for sampling biomolecules from skin is taking a skin swab. While desirable because of its simplicity, a skin swab is superficial in its depth of inspection, and qualitative in its results. Finally, tissue has been subjected to ultrasound in the presence of surfactants such as sorbitans ("SPANs"), polyoxyethelene sorbitans combined with fatty acids (Tween® surfactants), cetyl trimethylammonium bromide ("CTAB"), and their mixtures. See U.S. Pat. No. 6,589,173 issued to Mitragotri et al. However, SPANs, Tween® surfactants, and CTAB, individually and collectively, have been found to be unsuitable to recover skin constituents. Sorbitans and Tween® surfactants, which are nonionic surfactants, are mild and non-denaturing in character, but are ineffective to solubilize skin tissue. CTAB, a cationic surfactant, is effective to solubilize skin tissue, but unsuitably denatures proteins, profoundly changing properties of biomolecules in solution, rendering them unusable for functional purposes.

Thus, a need exists for compositions for skin sampling, as well as for mucosal membrane and other tissue sampling, which, when used in conjunction with applied energy, at least partially solubilize such skin, mucosal membrane, and other tissue. A further need exists to preserve the functionality and structural integrity of analytes, including biomolecules, obtained from the solubilized skin, mucosal membrane, and other tissue. A related need exists to remove surface lesions from skin and mucosal membranes, while preserving biomolecules obtained from the lesions for diagnosis or prognosis.

A further need exists for compositions and methods for solubilizing cells and other tissues (e.g., skin, liver, heart, brain, and other organs), and for the recovery of proteins, including cytosolic proteins, from the solubilized cells and tissues. Finally, a need exists for compositions and methods for fast and efficient solubilization and isolation of phosphoproteins from skin.

SUMMARY

In one embodiment, a method for treating a bacterial infection is provided, the method comprising administering an antibacterial composition, the antibacterial composition comprising 3-(decyl dimethyl ammonio) propane sulfonate and polyoxyethylene (4) lauryl ether.

In another embodiment, a method is provided for inhibiting the growth and reproduction of bacteria, the method comprising applying an antibacterial composition to an area that is subject to attack by the bacteria, the antibacterial composition comprising 3-(decyl dimethyl ammonio) propane sulfonate and polyoxyethylene (4) lauryl ether.

In another embodiment, a method is provided for solubilizing cells and/or tissue, the method comprising contacting the cells and/or tissue with a composition, the composition comprising 3-(decyl dimethyl ammonia) propane sulfonate and polyoxyethylene (4) lauryl ether. In one embodiment, proteins, including, for example, cytosolic proteins, nuclear proteins, and surface proteins, may be recovered from the solublized cells and/or tissue. In some embodiments, such as, for example, embodiments where it is desirable to preserve biological activity of the proteins, the composition may further optionally comprise a protease inhibitor.

In another embodiment, a method is provided for recovering cellular proteins, including, for example, signaling proteins, from skin cells, the method comprising: contacting the skin cells with a composition comprising 3-(decyl dimethyl ammonio) propane sulfonate and polyoxyethylene (4) lauryl ether to provide solubilized proteins; and subjecting the solubilized proteins to reverse phase protein array.

BRIEF DESCRIPTION OF THE DRAWINGS

In the accompanying figures, experimental data are given that, together with the detailed description provided below, describe example embodiments of the claimed invention.

DETAILED DESCRIPTION

Figure 1:
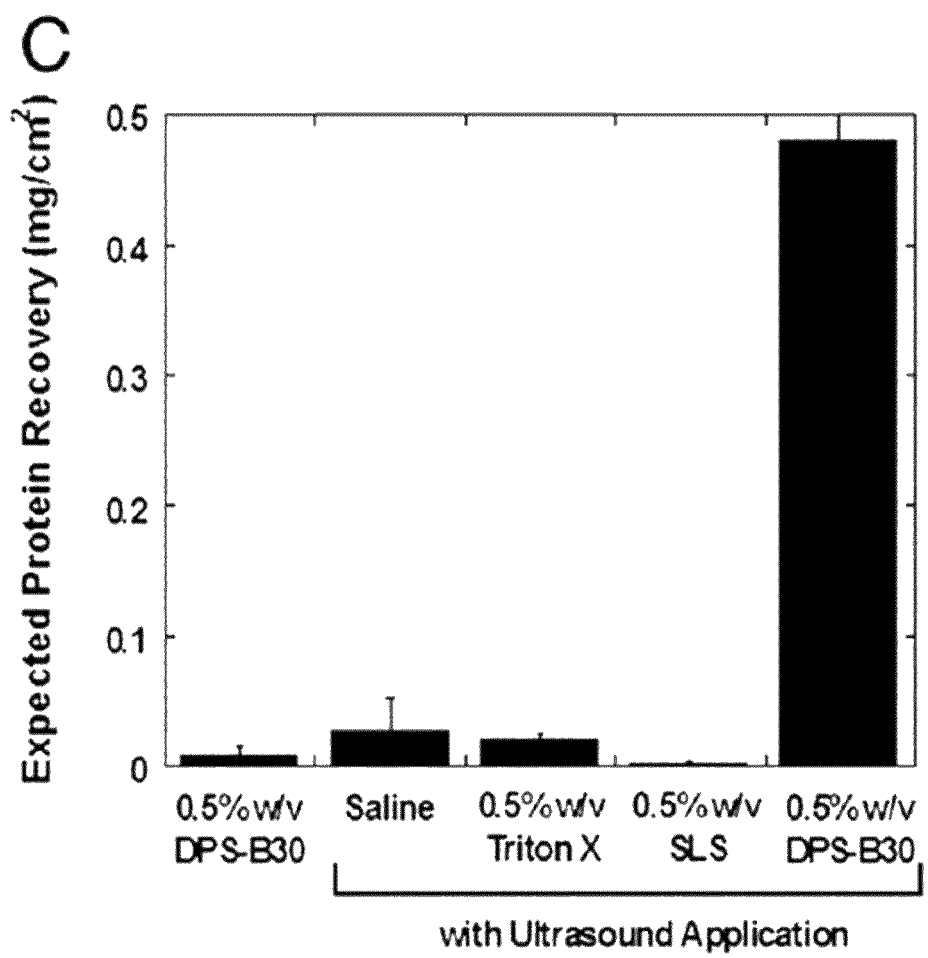
FIG. 1 illustrates a comparison of the expected functional protein recovery using DPS-B30 (0.5% (w/v)) with and without ultrasound application, with the expected functional protein recovery using saline, 0.5% (w/v) sodium lauryl sulfate ("SLS"), and 1% Triton-X-10 with ultrasound application.

The compositions and methods described herein are useful to solubilize and/or lyse target cells and tissue. The compositions and methods may further preserve proteins. This dual activity provides a clear advantage over current methods for dissolving tissue and collecting samples.

In one embodiment, a composition is provided, the composition comprising 3-(decyl dimethyl ammonio) propane sulfonate (DPS) and a polyethylene glycol dodecyl ether. In one embodiment, the polyethylene glycol dodecyl ether comprises polyoxyethylene (4) lauryl ether. In another embodiment, the polyethylene glycol dodecyl ether comprises "Brij 30" or "B30." The phrase "polyoxyethylene (4) lauryl ether" and "B30" are used interchangeably in this application, as polyoxyethylene (4) lauryl ether comprises the major component of the commercial surfactant B30 (also known as "Brij-30").

DPS is a zwitterionic surfactant:

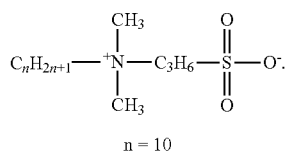

n = 10

Polyoxyethylene (4) lauryl ether is a nonionic surfactant:

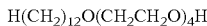

The DPS and the polyoxyethylene (4) lauryl ether may be dissolved in a buffer solution. The buffer solution may comprise, for example, one or more of phosphate-buffered saline (PBS) (pH=7.2-7.6), tris-buffered saline (pH=7.4-8.0), tris-hydrochloride (pH=7.0-9.0), and ethylenediaminetetraacetic acid (EDTA) (pH=7.4-9.0). The DPS and the 1330 may be present in a total concentration of between about 0.01% and about 10% (w/v) in the buffer solution. For example, the DPS and B30 may be present in a total concentration of about 0.01% to about 5% (w/v) in the buffer solution, including total concentrations of about 0.1% (w/v) to about 2% (w/v) in the buffer solution, about 1% (w/v) in the buffer solution, and about 0.1% (w/v) to about 0.5% (w/v) in the buffer solution. In one embodiment, the DPS and polyoxyethylene (4) lauryl ether are present in a total concentration of about 0.5% (w/v) in the buffer solution. In another embodiment, the DPS and the B30 may be present in a ratio of 3:2 to 2:3. In one embodiment, the DPS and the B30 may be present in a ratio of about 1:1.

The DPS:B30 composition has several applications. The composition may be used for solubilizing cells for in vitro protein recovery. In addition to effective dissolution of cells, the DPS:B30 composition may provide a benefit of preservation of bioactivity. The DPS:B30 composition may also possess the ability to quickly solubilize various tissues, including those with durable mechanical properties, such as skin. To aid in the preservation of bioactivity, a protease inhibitor may be included in the composition. However, with or without the addition of protease inhibitors, DPS:B30 may be able to preserve the biological activity of proteins. DPS:B30-based buffers are also applicable in vivo. In particular, DPS:B30-based buffer may be able to recover labile phosphoproteins with RPPA, thus opening the possibility of quickly and non-invasively probing multiple signaling pathways.

In some embodiments, solubilizing the target cells and tissue includes the application of energy. In some embodiments, the energy may be applied by any number of suitable methods, including mechanical (e.g., abrasion, shear, vacuum, pressure, suction, ultrasound), optical (e.g., laser), thermal, and electrical energy. However, in one embodiment, the energy does not include externally supplied thermal energy (i.e., heat). Suitable energy applicators are disclosed in U.S. patent application Ser. Nos. 12/664,994, 13/126,105, and 13/095,771, each of which is incorporated by reference herein in its entirety.

In one embodiment, the compositions may be useful as antibacterial compositions. Thus, a method for inhibiting the growth and reproduction of bacteria and/or treating a bacterial infection is provided, the method comprising administering an antibacterial composition, the antibacterial composition comprising 3-(decyl dimethyl ammonio) propane sulfonate and polyoxyethylene (4) lauryl ether.

In another embodiment, a method is provided for solubilizing cells and/or tissue, the method comprising contacting the cells and/or tissue with a composition, the composition comprising 3-(decyl dimethyl ammonio) propane sulfonate and polyoxyethylene (4) lauryl ether. In one embodiment, proteins, including cytosolic proteins, may be recovered from the solubilized cells and/or tissue. In some embodiments, such as, for example, embodiments where it is desirable to preserve biological activity of the proteins, the composition may further optionally comprise a protease inhibitor.

In one embodiment, the compositions may be used to probe protein functional states and related skin cell signaling pathways. Skin cell signaling pathways may be stress-induced, and may change over minutes to hours. Phosphorylation is a highly labile post-translational modification that regulates many aspects of protein function. The ability to probe these functional states in the epidermis necessitates a fast and efficient method to solubilize and isolate phosphoproteins. Thus, in another embodiment, a method is provided for recovering signaling proteins from skin cells, the method comprising: contacting the skin cells with a composition comprising 3-(decyl dimethyl ammonio) propane sulfonate and polyoxyethylene (4) lauryl ether to provide solubilized signaling proteins; and subjecting the solubilized signaling proteins to reverse phase protein array.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1: Protein Bioactivity Retention of DPS-B30

Mouse monoclonal Immunoglobulin E antibody (IgE; Catalog Number: MCA2259, AbD Serotec, Raleigh, N.C.) with functional binding specificity toward chicken albumin (OVA) was used as a model protein to demonstrate the protein bioactivity retention of DPS-B30 (0.5% (w/v)). Specifically, an enzyme-linked immunosorbent assay (ELISA) was performed to determine if IgE antibodies incubated in DPS-B30 retained their functionality to bind OVA specifically.

All ELISA reagents were purchased from KPL (Gaithersburg, Md.). Immulon-2 U-bottom polystyrene plates purchased from Dynex Laboratories (Chantilly, Va.) were coated with 100 μg OVA per well (1 mg/mL) in coating buffer for 1 h at room temperature. The plates were blocked with non-fat milk based blocking solution for 15 min. Test samples were generated by pre-incubating IgE antibody at 1 μg/mL with DBS-B30 for 1 hr, and loading on to the ELISA plate. The plates were incubated for 1 h at room temperature and washed three times with wash buffer. The plates were incubated with horseradish peroxidase-conjugated goat anti-mouse IgE antibody (2 μg/mL; Catalog Number: GE-90P-Z, ICL Inc., Newberg, Oreg.) for 1 h. The plates were washed four times with wash buffer, and treated with ABTS two-component substrate system. The absorbance was read at 405 nm 5 min after mixing of substrate.

The ELISA signal was corrected for non-specific background activity, obtained by omitting addition of IgE antibody. DBS-B30 bioactivity retention was compared with IgE dissolved in PBS as the positive control (100% bioactivity retention). DPS-B30 exhibited greater than 90% bioactivity retention.

Example 2: DPS-B30 Tissue Solubilization

Tissue solubilization was performed with surfactant (DBS-B30 (0.5% (w/v)) dissolution in conjunction with ultrasound. Porcine skin was used as a model tissue. The tightly packed and highly keratinized cellular environment of porcine skin tissue presents a formidable barrier to solubilization and, therefore, provided a suitable platform to perform solubilization studies. Porcine skin was frozen immediately after harvesting and shipped overnight over dry ice from Lampire Biological Laboratories Inc. (Pipersville, Pa.). The skin was stored at −70° C. until the experiment. Two hours before the experiment, skin was thawed at room temperature and cut into small pieces (2.5 cm×2.5 cm). Skin pieces stripped-off from subcutaneous fat and with no visible imperfections such as scratches and abrasions were used.

The solubilization experiment was carried out by mounting the skin piece on a Franz diffusion cell assembly (tissue exposure area of 1.77 cm$^2$; Permegear, Hellertown, Pa.). The receiver chamber of the diffusion cell was filled with PBS and the donor chamber was filled with 1 mL of DPS-B30 as the sampling buffer. DPS-B30 also acted as the coupling fluid between the ultrasound transducer and the tissue. Solubilization was performed at room temperature with a 600-Watt probe sonicator (Sonics & Materials, Newtown, Conn.) operating at a frequency of 20 kHz. The ultrasound transducer was placed at a distance of 5 mm from the tissue surface and an ultrasonic intensity of 2.4 W/cm$^2$ at 50% duty cycle was applied for 3 min. The sampling buffer, now containing solubilized tissue constituents, was aspirated and kept at −70° C. until analysis. The solubilization ability of DPS-B30 was quantified by the concentration of protein. Supernatants were isolated from solubilized skin using a centrifuge operating at 10,000 g and 4° C. for 15 min. Protein concentration of the supernatant was measured by using a colorimetric detection kit (Micro BCA Protein Assay Kit; Pierce, Rockford, Ill.). Protein concentration was determined by dividing the total protein content of the sample by the solubilized tissue area. DPS-B30 achieved protein solubilization of nearly 0.5 mg/cm$^2$.

FIG. 1 compares the expected functional protein recovery of DPS-B30 (0.5% (w/v)) with 0.5% (w/v) SLS, a surfactant commonly combined with ultrasound for transdermal drug delivery applications, and 1% Triton-X-10. Expected functional protein recovery is the product of fractional bioactivity retained and total solubilized protein. In addition to possessing only a moderate solubilization ability (0.07 mg/cm$^2$), SLS is highly denaturing, which results in a low functional protein recovery potential (~0.062 mg/cm$^2$). In contrast, DPS-B30 formulation not only solubilizes more skin proteins (0.48 mg/cm$^2$), but also preserves protein activity, resulting in an excess of 230-fold enhancement in functional protein recovery potential over SLS. Similarly, the ability of 0.5% (w/v) DPS-B30 to harvest functional proteins was more than 25-fold higher over 1% (w/v) Triton X-100.

When porcine skin was contacted with DPS-1330 (0.5% (w/v)) at a pH of about 8.8 in PBS, in the presence of ultrasound, the amount of soluble protein recovered increased to 0.33±0.02 mg/cm$^2$. The total protein recovered under these conditions was 0.86±0.15 mg/cm$^2$.

Example 3: Profiling of Sampled Proteins

DPS-B30 (0.5% (w/v)) was tested for its ability to preserve functionality of various types of proteins under ultrasonic exposure. Proteins (solubilization with 0.5% (w/v) DPS-830 formulation with in situ 3 min sonication) from porcine skin and mucosal tissues including colon, nasal, and buccal mucosa were characterized. Mucosal tissues were procured from Sierra for Medical Science Inc. (Whittier, Calif.). Tissues were frozen over dry ice immediately after harvesting and stored at −70° C. Sampling was performed by mounting the tissues on a Franz diffusion cell assembly. Tissue homogenate samples were also prepared for comparative analysis. Epidermal skin and mucosal membranes were gently scraped from the bulk tissues using a sharp scalpel and completely homogenized in 0.5% (w/v) DPS-B30 surfactant formulation using a mechanical homogenizer (Tissue Master-240, Omni International, Marietta, Ga.). An ice-bath was used to avoid temperature increase during homogenization. Care was taken to avoid scraping of the muscle and connective tissue underlying the mucosa. One dimensional SDS electrophoresis was performed under reducing conditions with 7.5% polyacrylamide gels (Bio-Rad Laboratories, Hercules, Calif.) and protein samples were adjusted to a final concentration of 2% SDS and 2% mercaptoethanol prior to loading. The protein migration patterns on fixed gels were stained with SYPRO® Ruby Protein Gel Stain reagent (170-3125, Bio-Rad Laboratories, Hercules, Calif.) and digitally imaged.

Figure 2A:
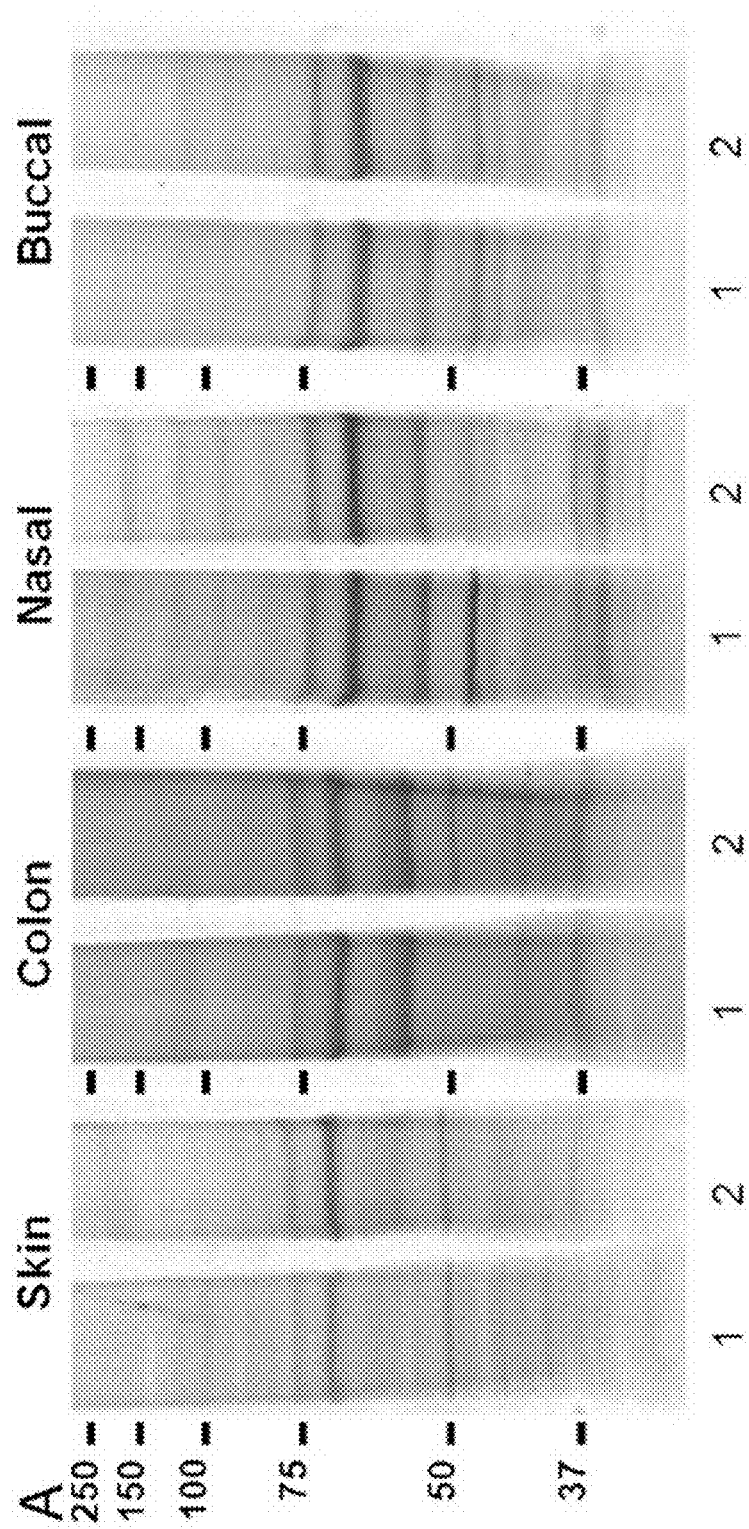
FIG. 2a illustrates a comparison of representative electrophoretic profiles of proteins present in various tissue samples solubilized using DPS-B30 (0.5% (w/v)) and mechanical agitation (lane 2), with profiles existing in respective homogenized skin and mucosal tissues (lane 1).

FIG. 2a illustrates representative electrophoretic profiles of proteins present in various samples (lane 2), which exhibit a high congruence with profiles existing in respective homogenized skin and mucosal tissues (lane 1).

Example 4: Assessment of Protein Bioactivity

A globular protein (IgE) and three enzymes (lactate dehydrogenase (LDH), beta-galactosidase (β-Gal), and lysozyme) were subjected to DPS-B30 (0.5% (w/v)) and sonication, and their bioactivity was monitored over time. In separate experiments, these proteins were added to 5 mL of DPS-B30 and the sample was transferred to a sonication chamber (centrifuge tube #430290, Corning Inc., Corning, N.Y.). Solubilization was performed at room temperature with a 600-Watt probe sonicator (Sonics & Materials, Newtown, Conn.) operating at a frequency of 20 kHz. The ultrasound transducer was placed at a distance of 5 mm from the tissue surface and an ultrasonic intensity of 2.4 W/cm$^2$ at 50% duty cycle was applied for 3 minutes. Proteins dissolved in PBS were prepared as comparative controls. Ultrasound (20 kHz, 2.4 W/cm$^2$, 50% duty cycle) was exposed for up to 6 min by lowering the probe transducer to a distance of 5 mm from the bottom of the chamber. 100 μL samples were periodically collected for analyzing protein bioactivity during ultrasound exposure. IgE functionality was assessed using the ELISA protocol described above; however, a more sensitive chemiluminescent substrate (LumiGLO; KPL, Gaithersburg, Md.) was used. LDH enzymatic activity was measured using a colorimetric assay kit according to manufacturer's guidelines (Catalog Number: G1780; Promega Corp., Fitchburg, Wis.). β-Gal enzymatic activity was also measured using a colorimetric assay kit according to manufacturer's guidelines (Catalog Number: 72134; Anaspec Inc., Fremont, Calif.). Samples were prepared at an initial concentration of 100 ng/mL IgE (MCA2259, AbD Serotec, Raleigh, N.C.), 1:500 dilution of LDH stock provided in the assay kit, 10 µg/mL β-Gal (G5635; Sigma Aldrich, St. Louis, Mo.), and 300 U/mL lysozome (L6876; Sigma Aldrich).

Figure 2B:
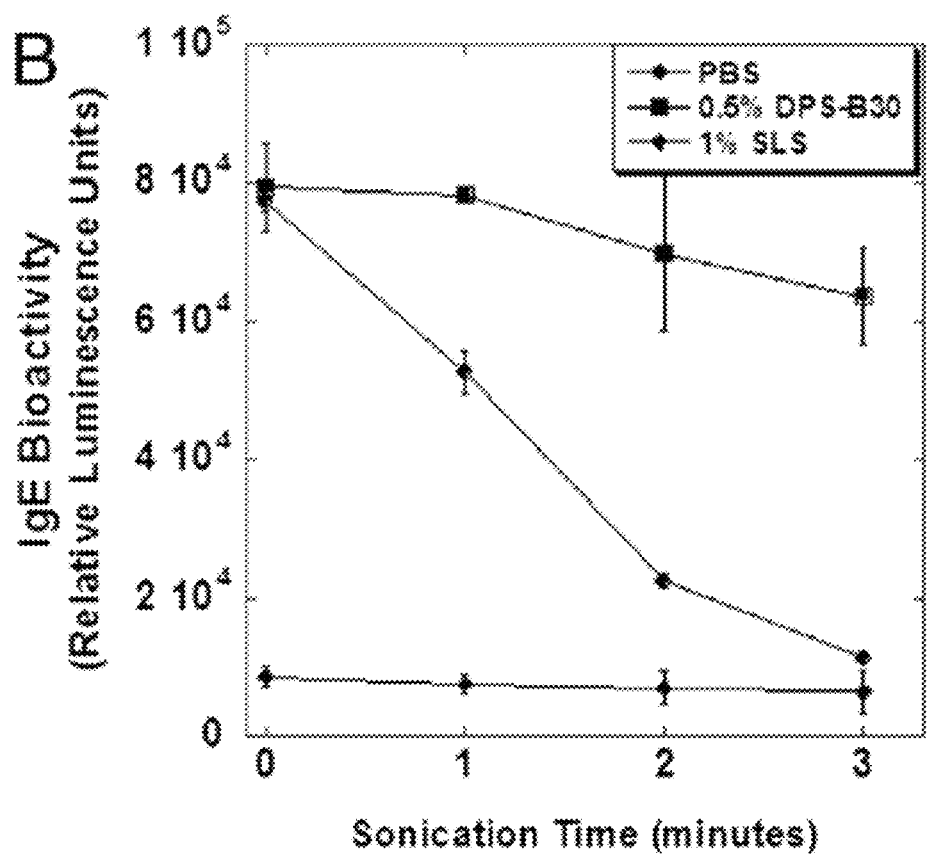
FIG. 2b illustrates a comparison of the effect on bioactivity of IgE proteins when the proteins were subjected to ultrasonic denaturing stress in various solubilizing compositions.

As shown in FIG. 2b, IgE remained functionally viable during the sampling procedure. The DPS-B30 formulation protected IgE proteins against ultrasonic denaturing stress. In contrast, a progressively sharp decrease in bioactivity was observed for IgE proteins prepared in PBS. Similarly, IgE prepared in SLS showed a complete state of denaturation.

Figure 2C:
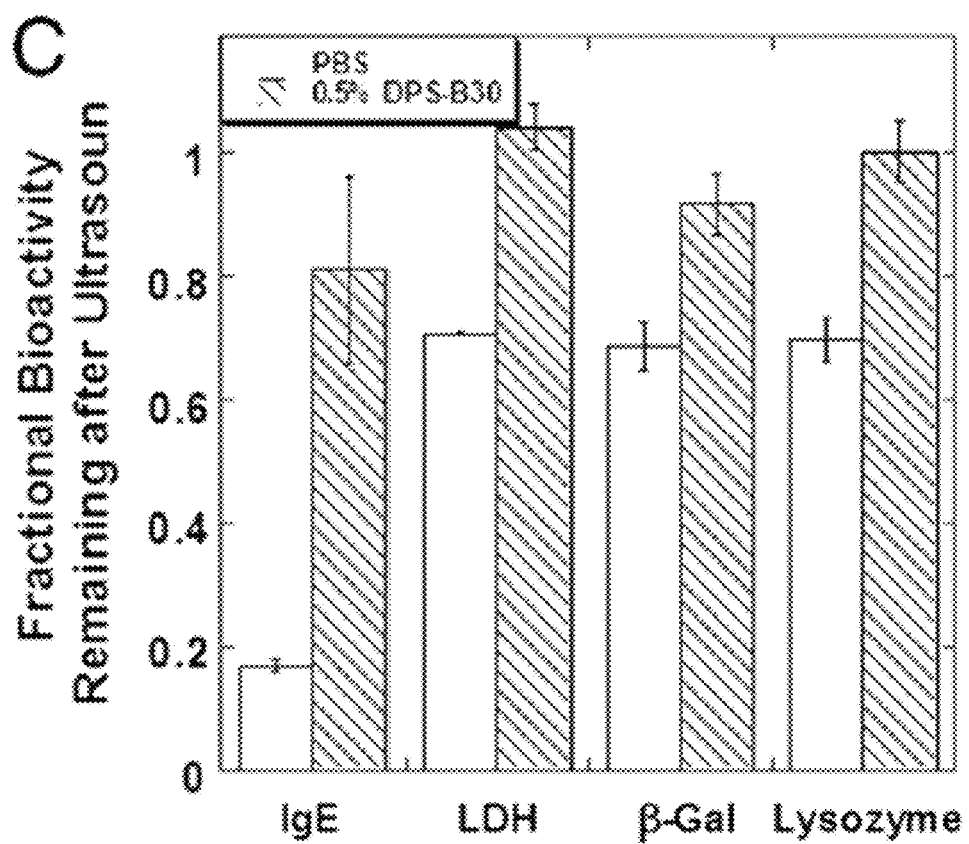
FIG. 2c illustrates a comparison of the effect on bioactivity of IgE, LDH, β-gal, and lysozyme when the proteins were subjected to ultrasonic denaturing stress using DPS-B30 (0.5% (w/v)) as a solubilizing composition versus using PBS.

As shown in FIG. 2c, preservation of fractional bioactivity for IgE, LDH, β-Gal, and lysozome proteins, when prepared in DPS-B30 formulation, was observed. Significant loss of bioactivity was observed for proteins prepared in PBS (open bars).

Example 5: Allergic Mouse Model

Allergy biomarkers (IgE antibodies) were extracted from eczematic skin and facilitated diagnosis of allergic dermatitis. Six to eight week old female BALB/CJ mice were purchased from Charles River Labs (Wilmington, Mass.) and maintained under pathogen-free conditions. All procedures performed on the mice were approved by the Institutional Animal Care and Use Committee of University of California, Santa Barbara, Calif. Allergic reaction was induced in mice by an epicutaneous exposure protocol. After anesthesia with 1.25-4% isofluorane in oxygen, the skin on the back of the mice was shaved and then tape stripped ten times by a 3M tape (3M Health Care, St Paul, Minn.) to introduce a standardized skin injury. A gauze patch (1 cm×1 cm) soaked with 100 µL of 0.1% OVA was placed on the back skin and secured with a breathable elastic cloth-based adhesive tape. The patches were kept affixed for 1 week. The whole experiment comprised a total of three 1-week exposures with a 2-week interval between each exposure week. A flanged chamber (skin exposure area of 1.33 $cm^2$) was glued to the shaven skin area with a minimal amount of cyanoacrylate-based adhesive. The chamber was filled with 1.8 ml of 0.5% DPS-B30 surfactant formulation and ultrasound was applied according to the operating parameters describe above. Skin biopsies of ultrasound treated or untreated eczema skin sites were obtained.

Figure 3:
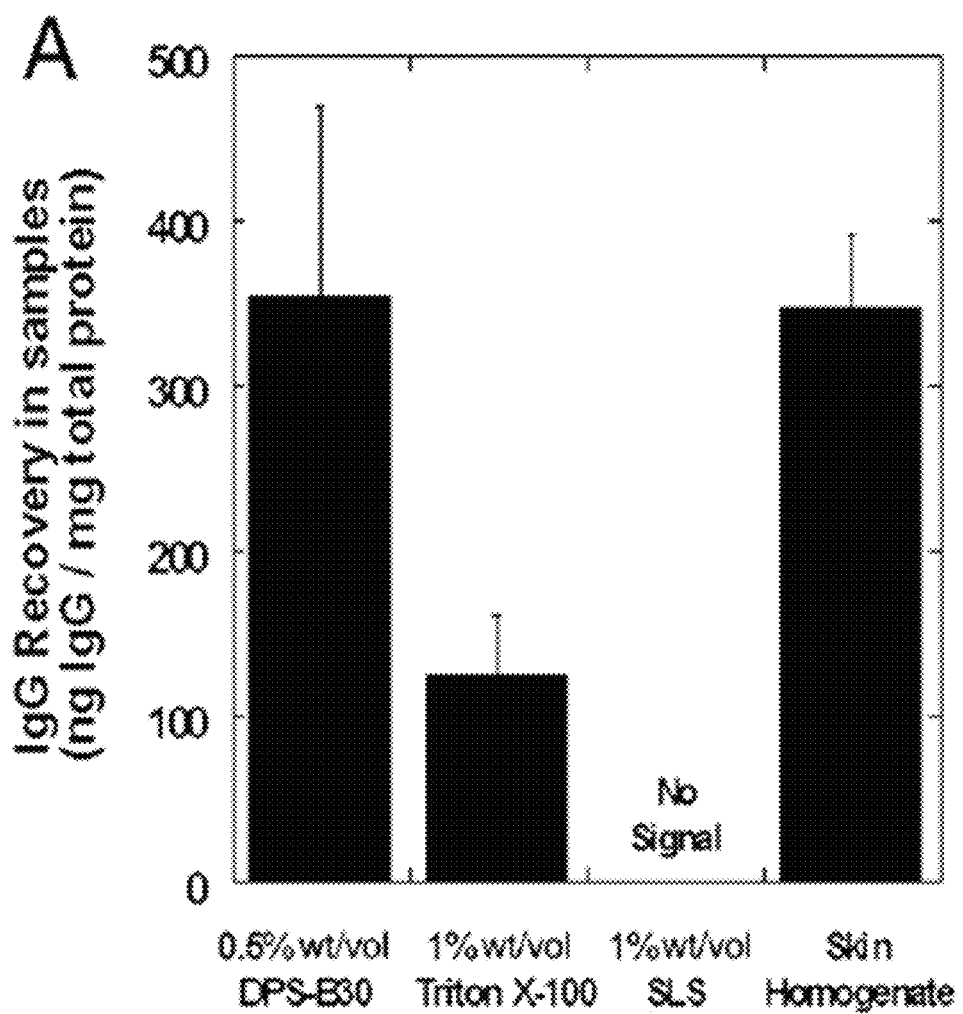
FIG. 3 illustrates a comparison of IgG recovery from mouse skin using various solubilizing compositions.

FIG. 3 illustrates that the extracted samples contained about a three-fold higher amount of IgE antibodies in allergic skin than healthy mouse skin. Consistent with the pathology of allergic disease, no statistically significant difference was found between the amounts of IgG antibodies in the samples obtained from allergic and healthy mice skin using 0.5% DPS-B30 surfactant formulation and ultrasound.

Example 6: Profiling and Quantification of Lipids

In addition to proteins, it was assessed whether the application of DPS-1330 and ultrasound can efficiently sample a multitude of lipids from tissues. Samples were prepared in vitro from excised porcine skin and mucosal tissues including colon, nasal, and buccal mucosa. Tissues were mounted on a Franz diffusion cell assembly and subjected to 3 min in situ sonication. Tissue homogenate samples were also prepared for comparative analysis. Lipids from each sample were extracted using the Bligh-Dyer method. After evaporating the solvent under a stream of nitrogen, lipid weight was estimated, and the lipids were reconstituted in 250 µL of chloroform/methanol (2:1) solvent for thin layer chromatography ("TLC") analysis. 10 cm long aluminum-backed TLC plates coated with a 200 µm-thick layer of silica gel (60 Å) (Merck-5554/7, EMD Chemicals, Gibbstown, N.J.) were washed with chloroform/methanol (2:1), air dried, and 20 µL of each lipid extract was applied at 1 cm distance from the bottom of the plate. The chromatograms were developed successively with hexane (to 9 cm), toluene (to 9 cm), and hexane/ether/acetic acid (70:30:1, twice to 5 cm). Cholesteryl stearate (cholesteryl esters, "CE"), triolein (triglycerides, "TG"), oleic acid (free fatty acids, "FA"), lanosterol ("LA"), and cholesterol ("CH") were spotted on TLC plates as reference standards. Lipids on the chromatographs were probed by charring with 8% $H_3PO_4$ solution containing 10% w/v $CuSO_4$ and 5% v/v methanol, followed by slow heating at 180° C. in an oven until a good contrast was obtained.

Figure 4A:
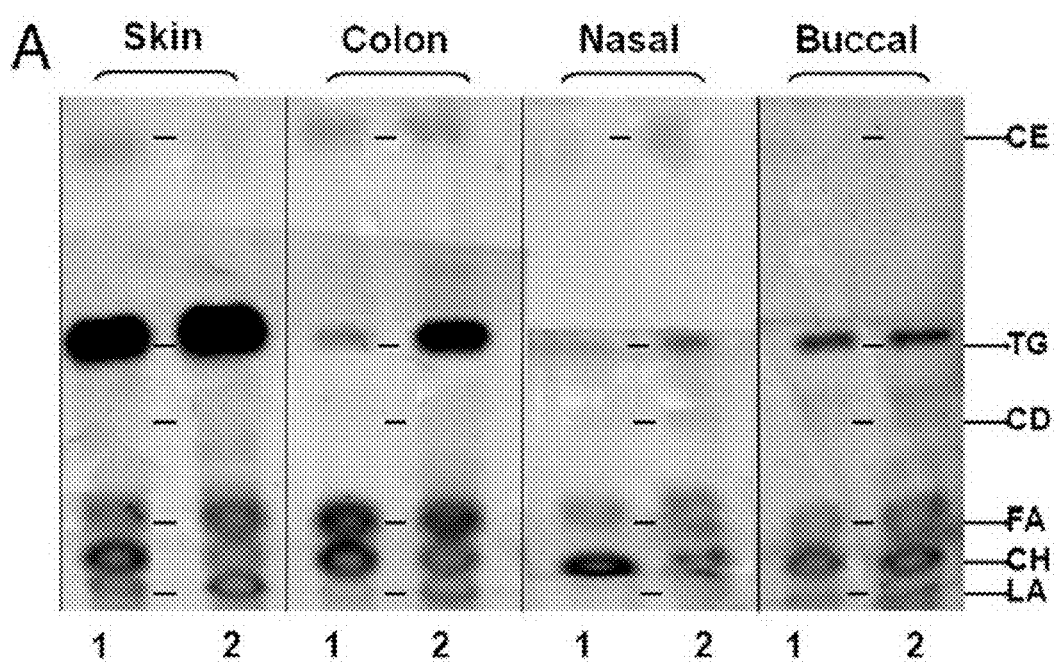
FIG. 4a illustrates a comparison of non-polar lipids extracted from porcine skin and mucosal tissues using DPS-B30 (lane 2), with the lipid profiles in tissue homogenate samples (lane 1).
Figure 4B:
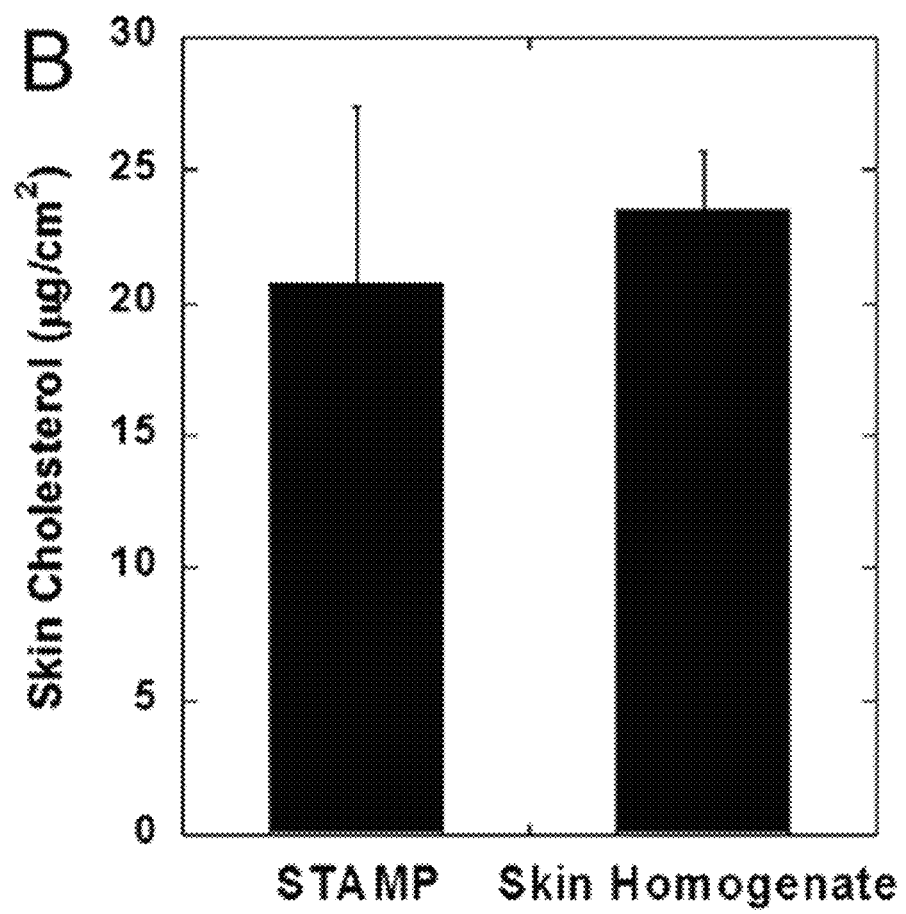
FIG. 4b illustrates a comparison of the results of in vivo sampling of mouse skin for cholesterol sampled using DPS-B30 and ultrasonic applied energy, with the actual amount of cholesterol natively present in the skin.

The chromatographs in FIG. 4a illustrate that DPS-B30 (lane 2) was able to retrieve all major types of non-polar lipids from porcine skin and mucosal tissues in vitro, which compared well with the lipid profiles in tissue homogenate samples (lane 1). Six types of lipids were sampled: CE, TG, cholesteryl diesters (CD), FA, CH, and LA. The sampling efficiency was further quantified in vivo using mice. In vivo sampling of mouse skin showed that the amount of cholesterol sampled from skin using ultrasound and DPS-B30 was representative of the actual amount of cholesterol natively present in skin (FIG. 4b). Since cholesterol quantification necessitated structural integrity and chemical stability of the cholesterol molecule, it may be inferred that DPS-B30 and applied energy effectively sampled, and preserved, the functionality of cholesterol.

Example 7: Sampling of Genomic DNA

Samples were prepared from excised porcine skin using 0.5% (w/v) DPS-B30 surfactant formulation and a brief in situ 3 min sonication. Skin was mounted on a Franz diffusion cell assembly. As a comparative control, samples were obtained by swabbing the skin with cotton swabs (B4320115, BD Diagnostics, Franklin Lakes, N.J.). A sterile metal ring (area of 3.3 $cm^2$) was clamped onto the skin surface and sampling was restricted by swabbing skin enclosed within the ring. Swabs were soaked in sterile PBS and gently rubbed against the skin surface for 20 seconds. Each swab was extracted with 1 mL PBS solution for 1 h. Samples were also obtained by scraping skin. A sterile metal ring was firmly held against the skin surface and 1 mL of 0.1% (w/v) TritonX-100 in 0.075 M phosphate buffer, pH 7.9, was dispensed onto the skin surface. The skin surface within the ring was rubbed firmly for 1 min with a Teflon cell scraper and the resulting sample was collected. The procedure was repeated at the same skin site for two additional times and the samples were pooled together. Bacterial genome was purified from each sample by standard phenol-chloroform extraction method. The samples were first incubated in a solution comprising 20 mM Tris at pH 8.0 (BP154, Fisher Scientific, Fairlawn, N.J.), 2 mM EDTA (BP120, Fisher Scientific), 1.2% Triton X-100 (BP151-100, Fisher Scientific), and 20 mg/mL lysozyme (62970, Sigma Aldrich, St. Louis, Mo.) for 30 min at 37° C. Samples were incubated for 3 hours at 37° C. in a solution comprising 0.1 mg/mL Proteinase K (P2308, Sigma-Aldrich), 0.5% (w/v) sodium lauryl sulfate (S529, Fisher Scientific), and 100 mM sodium chloride (BP358, Fisher Scientific). Genomic DNA was extracted with an equal volume of phenol (P4557, Sigma-Aldrich), followed by extraction with phenol/chloroform/isoamyl alcohol, 25:24:1 (P2069, Sigma-Aldrich). The DNA was precipitated by incubation with ethanol and centrifugation for 20 min. The DNA pellets were washed twice with 70% ethanol, allowed to dry, and re-suspended in 80 µL of tris buffer. To quantify the amount of bacteria in each sample, real-time quantitative PCR was performed based on an amplicon of the conserved 16S rRNA bacterial gene. Analysis of the 16S gene was performed on the iCycler PCR machine (Bio-Rad Laboratories, Hercules, Calif.) using optical grade 96-well plates. Bacterial 16S gene was amplified using forward primer 63F (5'-22AGAGTTTGATC-CTGGCTCAG-3') and reverse primer 355R (5'-GACGGGCGGTGTGTRCA-335, 41). For each sample, 10 µL of purified genomic DNA was mixed with 2 pmol of each primer and Platinum PCR Supermix (11784, Invitrogen, Carlsbad, Calif.) to a final reaction volume of 20 µL. Thermal cycling was set as follows: Initial denaturation at 94° C. for 5 min, followed by 32 cycles of a 30 sec 94° C. denaturation, 30 sec annealing at 66° C., and 30 sec elongation at 72° C., all followed by a final extension of 10 min at 72° C. To calibrate the number of bacteria in each sample, a standard curve was constructed by amplifying serial dilutions of genomic DNA from known quantities of $E.$ $Coli$ cells in 10 µL of tris buffer.

Additional experiments were conducted to evaluate the structural integrity of bacterial DNA under sonication stress. Bacterial culture of $E.$ $Coli$ strain DH10α (18290-015, Invitrogen) were grown in Luria-Bertani (BP1426, Fisher Scientific) at 37° C., 250 rpm. $E.$ $Coli$ cells were quantified with a spectrophotometer (Biophotometer, Eppendorf, Hauppauge, N.Y.), and a bacterial culture of $0.25 \times 10^9$ cells/mL was considered to correspond to an optical density absorbance value of 0.25 at a wavelength of 600 nm. Culture was harvested by centrifugation and the resulting pellet was suspended in either tris buffer (10 mM Tris-HCl, pH 7.9) or 0.5% (w/v) DPS-B30 surfactant formulation at a concentration of $10^9$ cells/mL. One mL of cell suspension was placed in a sterilized sonication chamber (centrifuge tube #430290, Corning Inc., Corning, N.Y.). Sonication (20 kHz, 2.4 W/cm$^2$, 50% duty cycle, 3 min) was performed by lowering the probe transducer to a distance of 5 mm from the bottom of the chamber. After sonication, genome DNA was purified from each sample using the DNeasy DNA Extraction Kit (69504, Qiagen, Valencia, Calif.). The purified genomic DNA was re-suspended in 400 µL of Buffer AE and subjected to electrophoresis for 90 min at 100 V in a 2% (w/v) Tris-acetate-EDTA-agarose gel. The gels were stained with SYBR Gold (S11494, Invitrogen) and visualized under UV light.

Figure 4C:
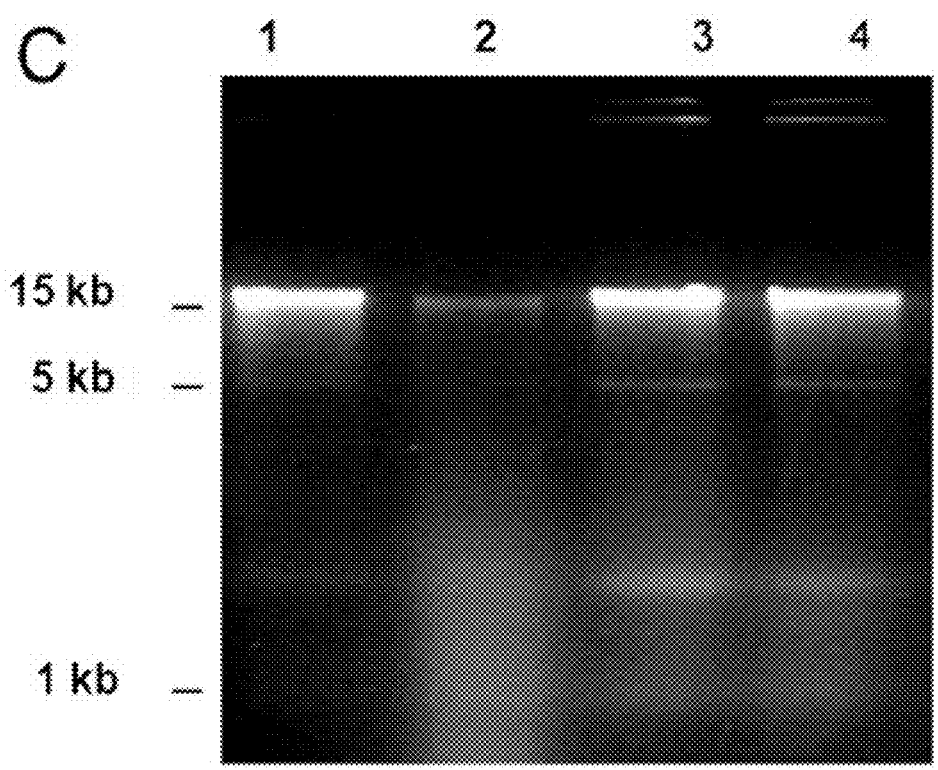
FIG. 4c illustrates the effect of sonication on bacterial DNA prepared in TBS (lane 2) compared to non-sonicated bacterial suspension in TBS (lane 1), non-sonicated bacterial suspension in DPS-830 (lane 3), and sonicated bacterial suspension in DPS-B30 (lane 4).

FIG. 4c illustrates that sonication significantly damaged bacterial DNA prepared in TBS (lane 2) compared to non-sonicated bacterial suspension in TBS (lane 1) or in DPS-B30 (lane 3). In contrast, DPS-B30 surfactant formulation (lane 4), when added to the bacterial suspension, provided outstanding protection to DNA's structural integrity from denaturing stress of the sonication procedure. This is consistent with preservation of the bioactivity of proteins with DPS-B30 formulation (FIG. 2c).

Example 8: Localized Transport Regions

Figure 5A:
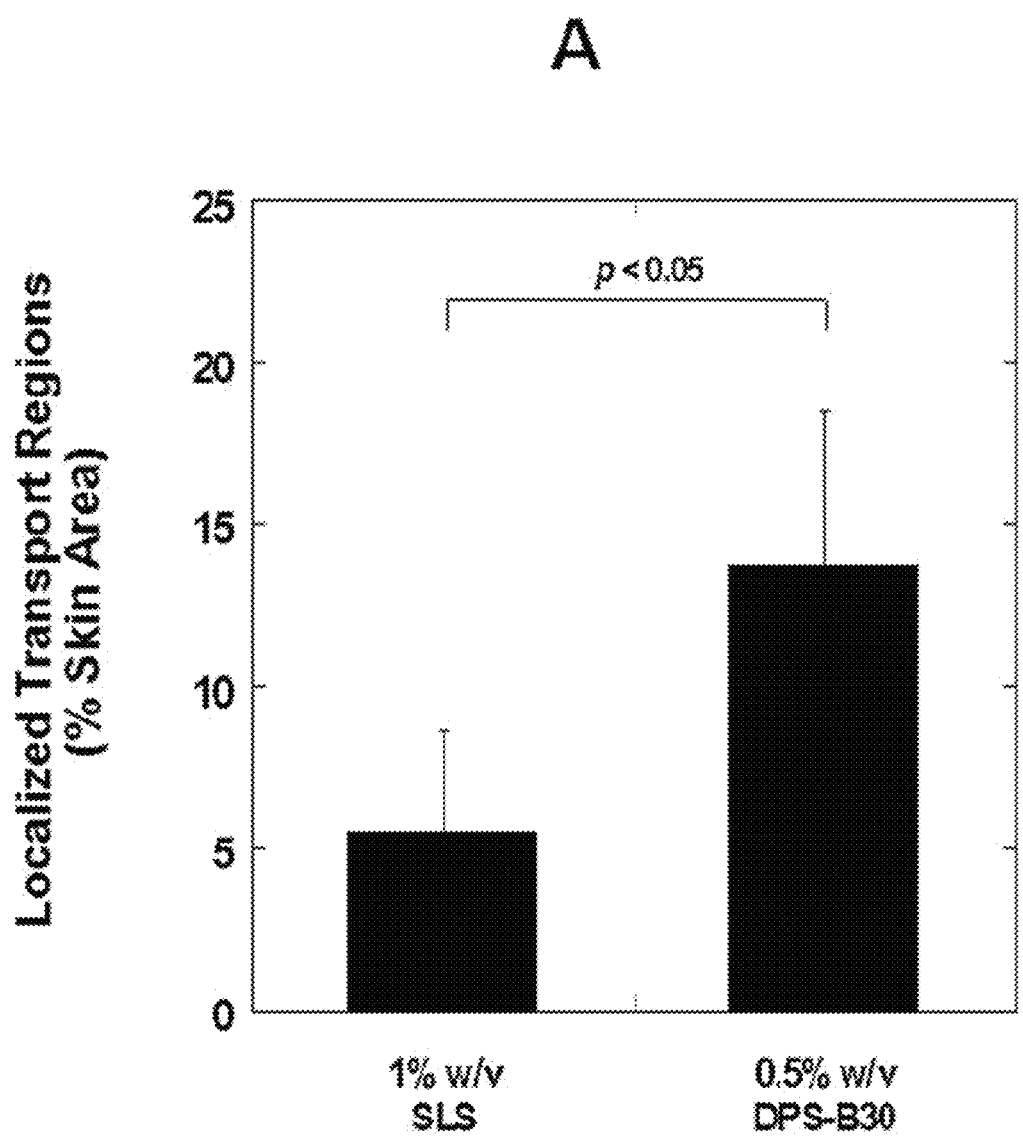
FIG. 5a illustrates a comparison of the localized transport region ("LTR") area of skin treated with ultrasound and 0.5% (w/v) DPS-B30, with the LTR area of skin treated with ultrasound and 1% (w/v) SLS.
Figure 5B:
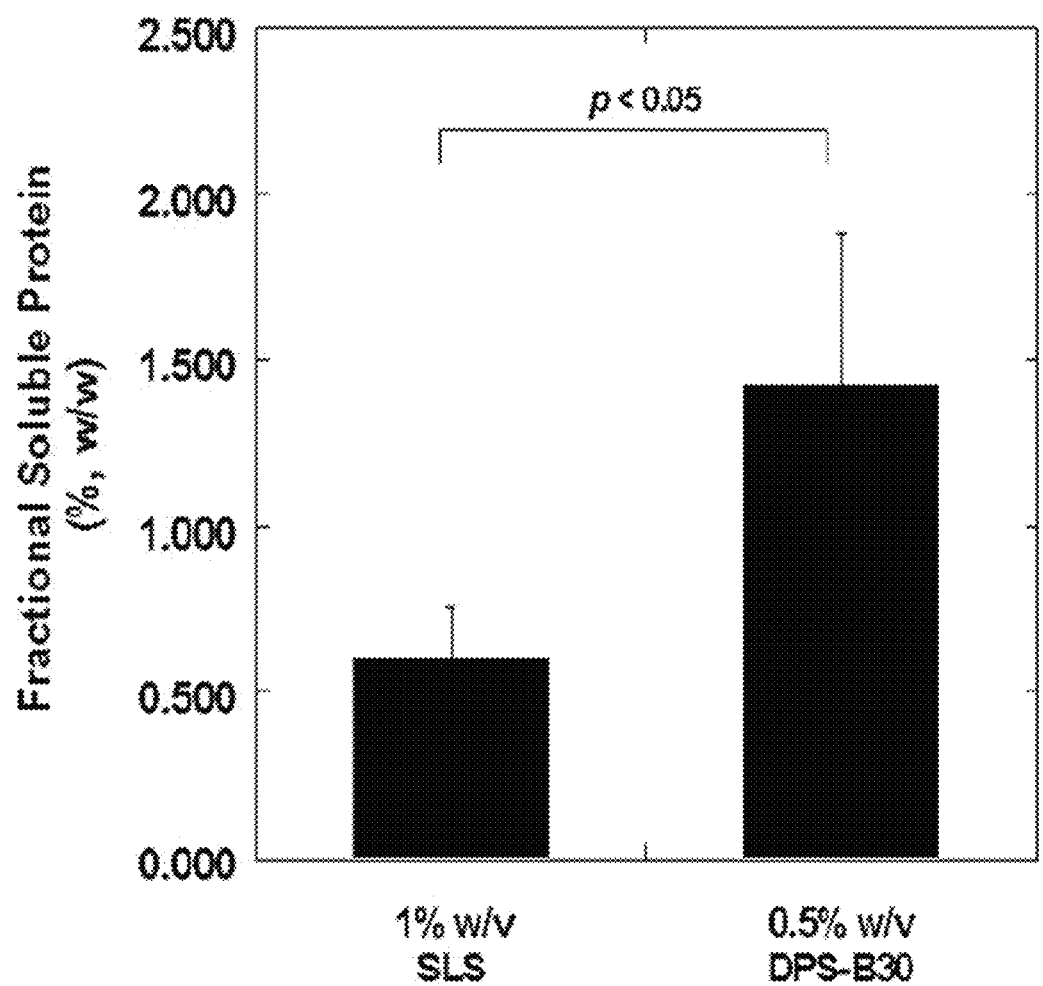
FIG. 5b illustrates a comparison of the proportion of soluble protein in a sample of skin treated with ultrasound and 0.5% (w/v) DPS-B30, with the proportion of soluble protein in a sample of skin treated with ultrasound and 1% (w/v) SLS.

Increased sampling of functional tissue constituents as described herein is a compounded result of the unique and unexpected ability of DPS-B30 to solubilize molecules from tough tissue assemblies, as well as to retain molecular bioactivity despite applied energy, such as sonication stress. The effect of surfactant and applied energy on skin, however, is highly localized, leading to the formation of LTRs. Application of ultrasound to skin with 0.5% (w/v) DPS-B30 may lead to at least a 3-fold enhancement of area of LTRs compared to that from 1% (w/v) SLS (FIG. 5a). Additionally, DPS-B30-ultrasound combination yielded about a 3-fold higher proportion of soluble protein in the sample compared to that yielded by SLS-ultrasound combination (FIG. 5b). Collectively, these results indicate that for a given ultrasound condition, DPS-B30 formulation provides dramatically and unexpectedly higher recovery of solubilized protein compared to that by SLS.

Figure 6A:
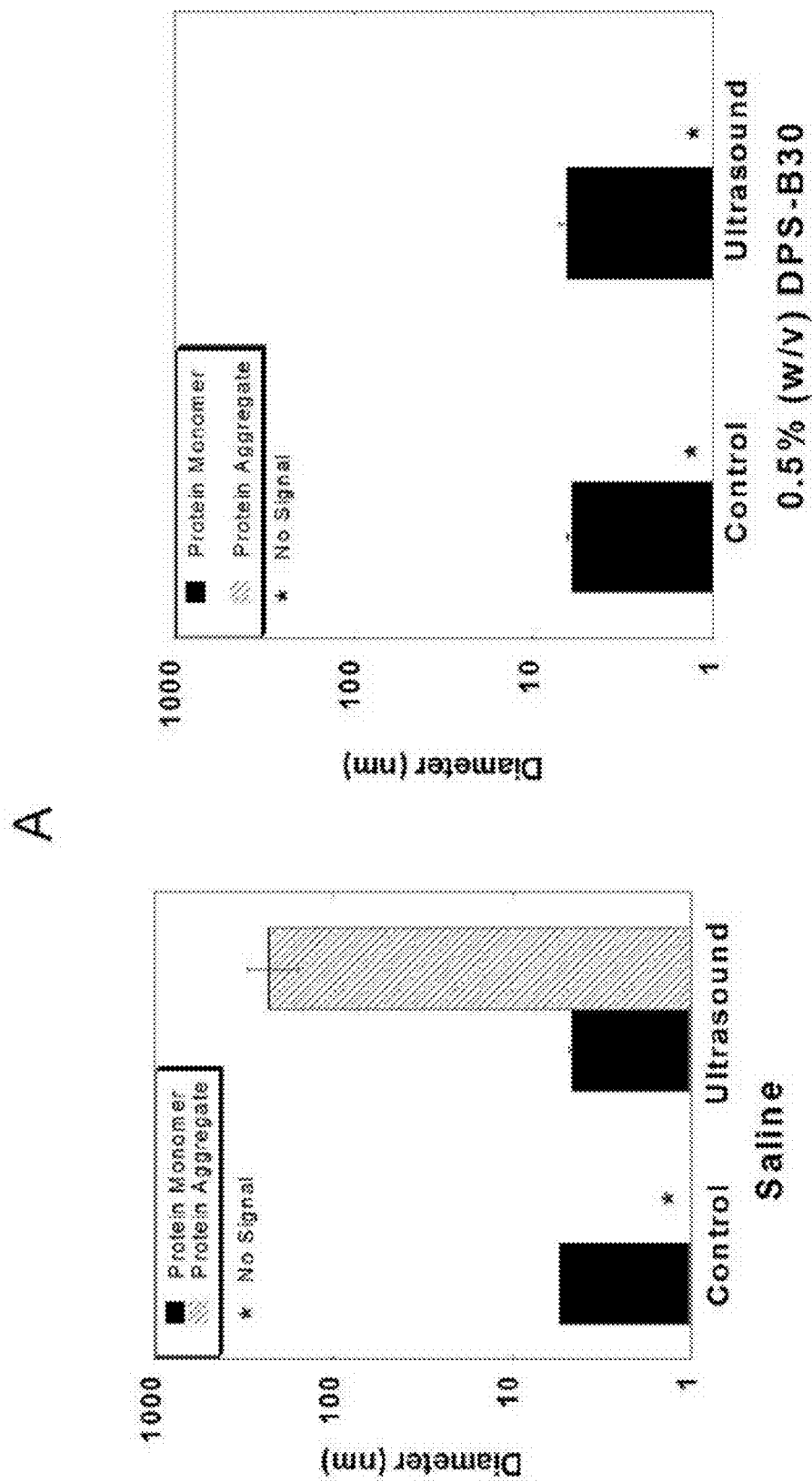
FIG. 6a illustrates a comparison of the diameter of lysozyme that has been solubilized in saline and subjected to ultrasound, with lysozyme that has been solubilized in 0.5% (w/v) DPS-B30 and subjected to ultrasound.
Figure 6B:
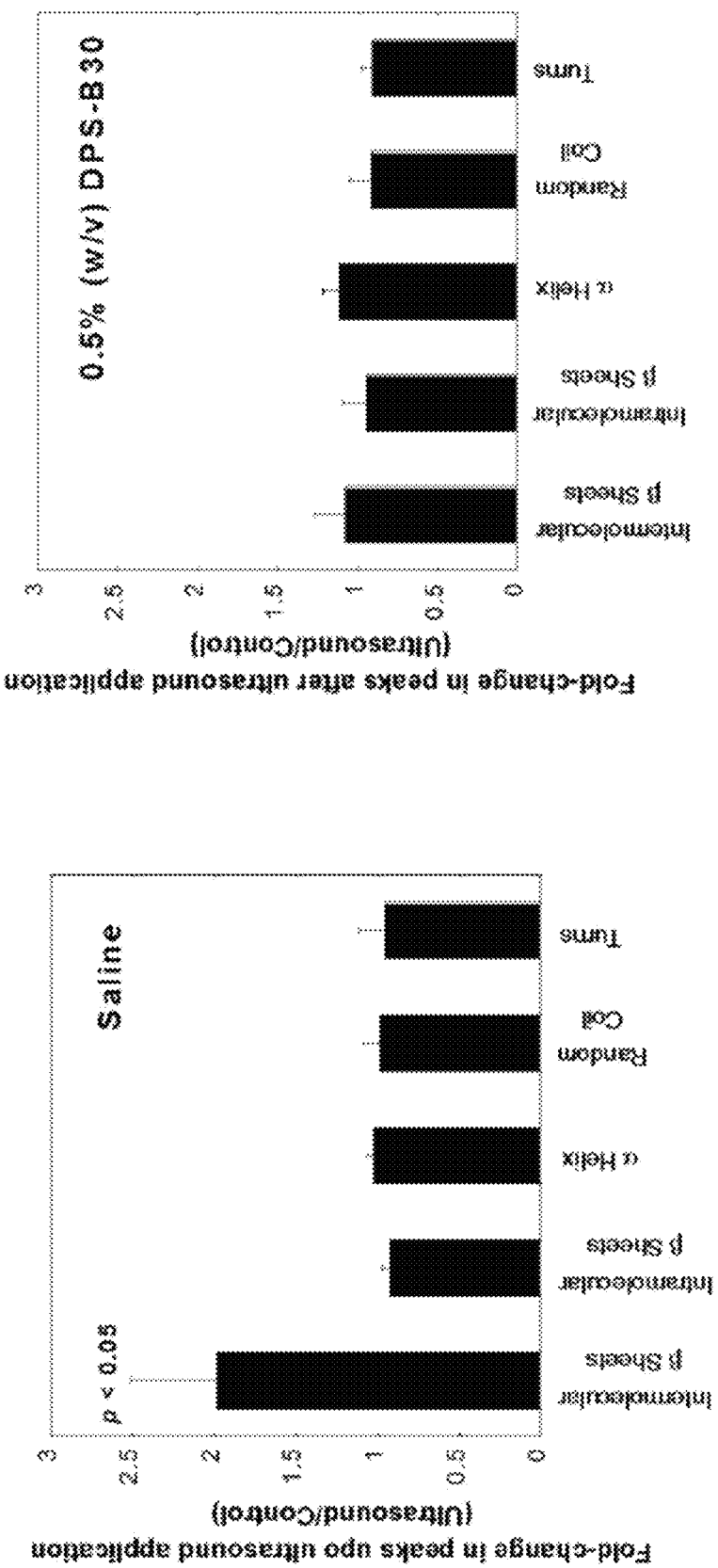
FIG. 6b illustrates a comparison of the rearrangement of β-sheets (from intramolecular to intermolecular β-sheets) observed after sonication of lysozyme prepared in saline, with the rearrangement observed after sonication of lysozyme prepared in 0.5% (w/v) DPS-B30.

The benefits of DPS-B30 are further escalated by its ability to preserve the protein structure. Unlike SLS, DPS-B30 prevents protein denaturation on its own. In addition, DPS-B30 protects proteins against ultrasound-induced denaturation. Dynamic light scattering and FT-IR spectroscopy studies were performed to obtain insight into this behavior. Lysozyme was used as a model protein because of its availability in pure and large quantities, and its well-characterized behavior in aqueous solution. Light scattering studies revealed that lysozyme, when solubilized in saline, rapidly forms large aggregates when subjected to ultrasound (aggregate size of 229.5±72 nm compared to native size of 5.4±0.01 nm; FIG. 6a). In contrast, lysozyme prepared in 0.5% (w/v) DPS-B30 surfactant formulation did not aggregate when exposed to ultrasound. Direct measurement of lysozyme bioactivity and FT-IR studies (FIG. 6b) confirmed these findings. A significant rearrangement of β-sheets (from intramolecular to intermolecular β-sheets) was observed after sonication of lysozyme prepared in saline. Increased content of intermolecular β-sheets is the most prominent change in the secondary structure of aggregated proteins and is commonly found in proteins subjected to thermal, chemical, or physical stress. Rearrangement of β-sheets to intermolecular conformation without grossly changing the secondary protein structure is expected. Physical shearing, similar to cavitation-induced forces experienced by protein under ultrasound exposure, has been shown to disrupt protein's native fold, but leave secondary structural elements intact and thereby enhance intermolecular interactions and aggregation. Notably, formation of aggregates and increase in the intermolecular β-sheets for several proteins (including lysozyme) subjected to low-frequency ultrasound have been reported. Consistent with the absence of aggregates (found by light scattering), no change in the intermolecular β-sheet content was observed when DPS-B30 surfactant formulation was added during sonication of lysozyme (FIG. 6b). These results demonstrate the ability of DPS-B30 to prevent protein aggregation.

Example 9: Preparation of Test Compositions (DB-1, DB-2, TX-1, and TX-2)

DPS was procured from Sigma-Aldrich and 1330 was procured from TCI America. DB-1 was prepared by adding 0.25% w/v DPS and 0.25% v/v B30 in PBS (pH 7.4). DB-2 was prepared by adding complete protease inhibitor cocktail tablets (Roche Applied Science, IN, USA) to DB-1 (a tablet per 50 ml; one tablet contains Antipain-dihydrochloride 3 mg, Aprotinin 0.5 mg, Bestatin 0.5 mg, Chymostatin 1 mg, E-64 3 mg, EDTA-Na$_2$ 10 mg, Leupeptin 0.5 mg, Pefabloc SC 20 mg, Pepstatin 0.5 mg, and Phosphoramidon 3 mg). A positive control was prepared comprising 1% v/v Triton X-100 (TX-1) in 50 mM HEPES (pH=7.4), 150 mM NaCl, 1.5 mM MgCl$_2$, 1 mM EGTA, 100 mM NaF, 10 mM Na pyrophosphate, 10% glycerol, freshly added by 1 mM Na$_3$VO$_4$. An additional positive control (TX-2) was prepared by adding complete protease inhibitor cocktail tablets (Roche Applied Science, IN, USA) in TX-1 (a tablet per 50 ml).

Example 10: Cell Solubilization

HEK cells (HEKa-APF, Invitrogen, CA, USA) and pooled HUVECs (Invitrogen, CA, USA) were cultured in a Corning® cell culture treated flask with Vent Cap (75 cm$^2$ Rectangular Canted Neck, Corning). HEK cells were grown between passages 3 to 8 in an EpiLife® Medium with 60 µM calcium added by Human Keratinocyte Growth Supplement. HUVECs were grown between passages 3 to 5 in a Medium 200 supplemented with Low Serum Growth Supplement.

Figure 7:
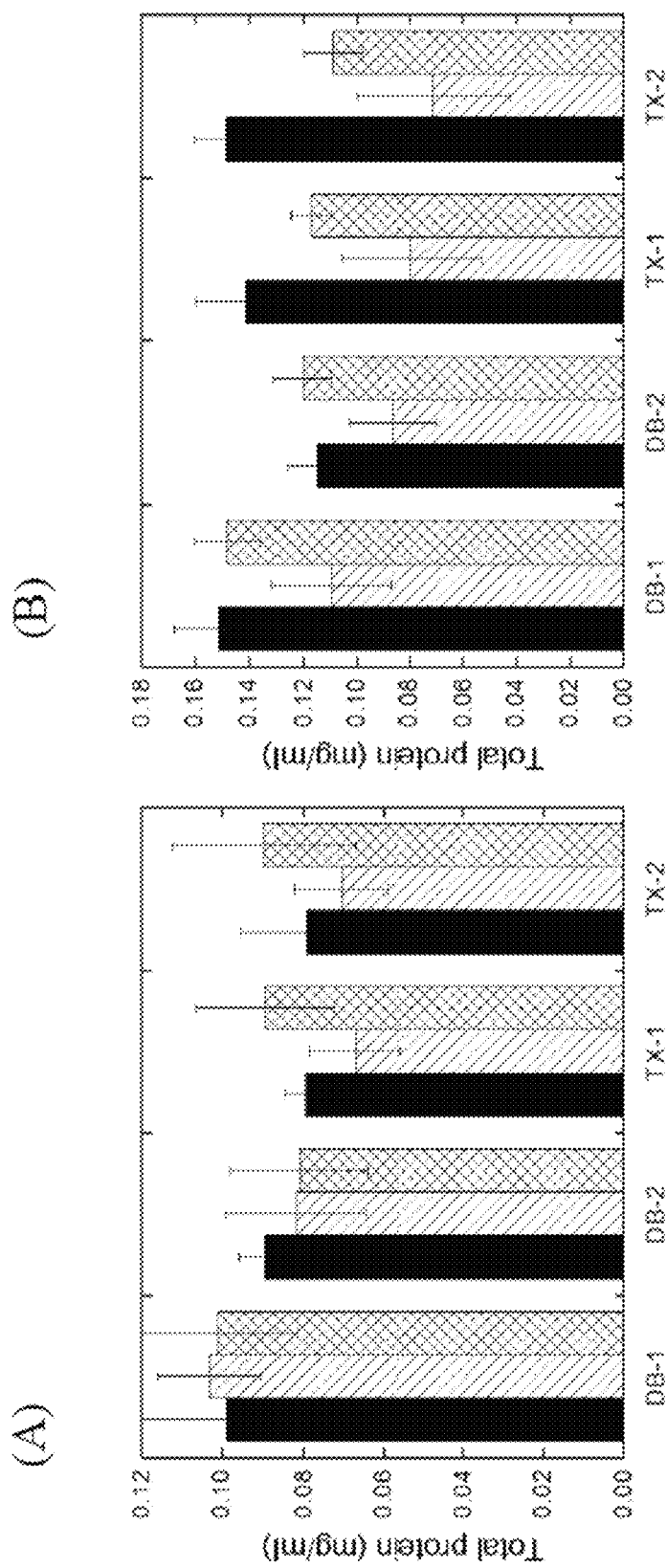
FIG. 7 illustrates the recovery of proteins using various reagents from (A) Human Umbelical Vein Endothelial Cells (HUVECs) and (B) Human Epidermal Keratinocyte (HEK) cells at t=0 (solid bars), t=4 hours at 4° C. (diagonal bars), and t=4 hours at RT (cross-hatched bars).

FIG. 7 illustrates the recovery of proteins using DB-1, DB-2, TX-1, and TX-2 from (A) HUVECs and (B) HEK cells at t=0 (solid bars), t=4 hours at 4° C. (diagonal bars), and t=4 hours at RT (cross-hatched bars). DB-1 and DB-2 were effective in solubilizing both cell types. No major differences were found in protein recovery with TX-based or DPS:B30-based reagents. The amount of proteins recovered from the cells was somewhat better maintained for 4 h at RT compared to that at 4° C.

Example 11: In Vitro Assay

The activity of GAPDH and LDH was assessed. KDalert™ GAPDH Assay Kit (Ambion, Inc, TX, USA) was used for analysis of GAPDH. CytoTox 96® Non-Radioactive Cytotoxicity Assay (Promega, WI, USA) was used for LDH analysis. Total protein in solubilized cells was analyzed using a Micro BCA Protein Assay Kit (Fisher Scientific, PA, USA). Trypsinized cells were counted by hemocytometer (Fisher Scientific, PA, USA) and added to 96-well plates. After overnight growth, the media was removed and replaced by 100 µl of lysis agents (DB-1, DB-2, TX-1, or TX-2). Cells were kept in contact with the lysis agent either for: (i) 30 min for RT, (ii) 4.5 h at RT, or (iii) 4.5 h at 4° C.

Figure 8:
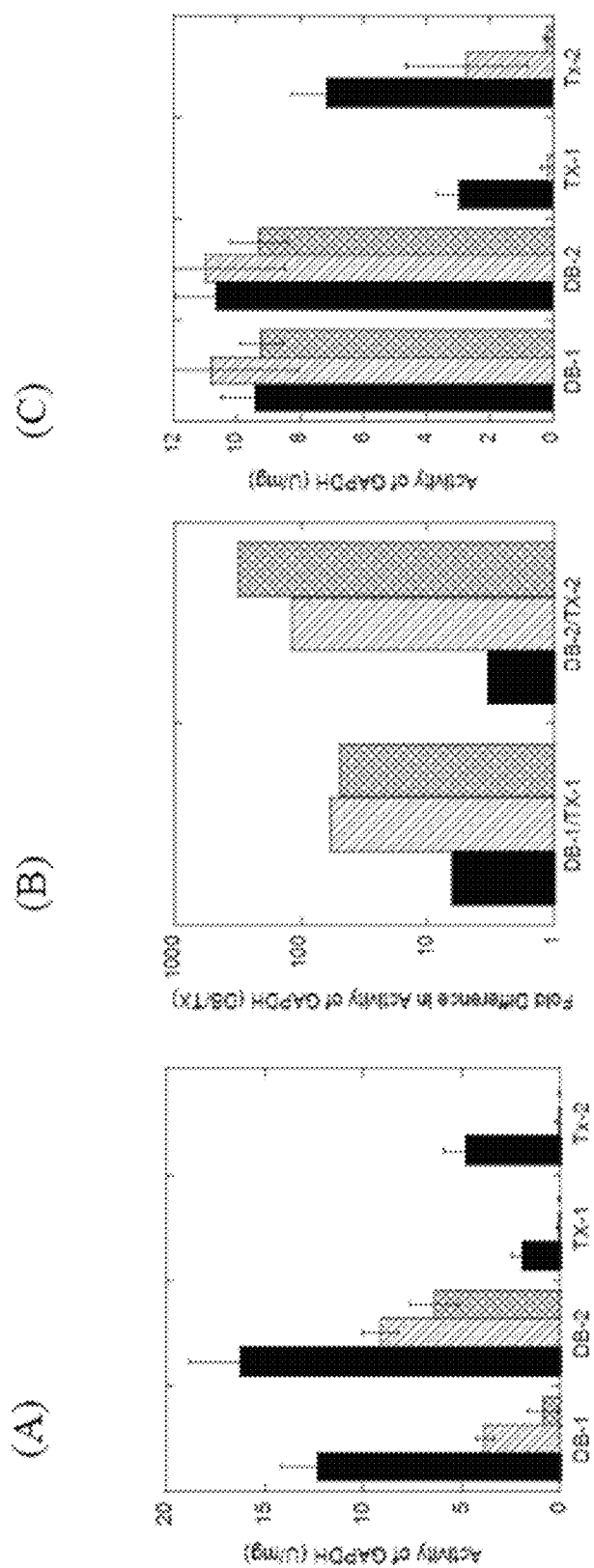
FIG. 8 illustrates (A) the preserved activity of the intracellular enzyme glyceraldehyde 3-phosphate dehydrogenase (GAPDH) in proteins extracted using various reagents from HUVECs, (B) fold difference of various reagents for HUVECs, and (C) the preserved activity of GAPDH in proteins extracted using various reagents from HEK cells, at t=0 (solid bars), t=4 hours at 4° C. (diagonal bars), and t=4 hours at RT (cross-hatched bars).

FIG. 8 illustrates (A) the preserved activity of GAPDH in proteins extracted using various reagents from HUVECs, (B) fold difference of various reagents for HUVECs, and (C) the preserved activity of GAPDH in proteins extracted using various reagents from HEK cells, at t=0 (solid bars), t=4 h at 4° C. (diagonal bars), and t=4 hours at RT (cross-hatched bars).

GAPDH was detected in cells solubilized by all reagents; however, the amount of active enzyme varied among various agents. In HUVECs, DB-1 yielded 12.3 U of GAPDH per mg of protein (FIG. 8(A)). The amount of active enzyme decreased with time with ~31% of active GAPDH remaining after storage of the cell extract for four hours at 4° C. Even more GAPDH was lost when the cell extracts were stored at room temperature. Loss of GAPDH during storage was mitigated when protease inhibitors were added to the reagent (DB-2, FIG. 8(A)). The amount of active GAPDH in DB-1 and DB-2 under any given condition was significantly higher than in TX-1 and TX-2 under corresponding conditions (DB-2, FIG. 8(A)). The differences were particularly higher at four hours (DB-2, FIG. 8(A)). At zero time, DB-1 and DB-2 yielded 6.4 and 3.4 fold higher GAPDH compared to TX-1 and TX-2, respectively. These differences increased to >50-fold at 4 h for DB-1 as well as DB-2. Similar observations were made for HEK cells (FIG. 8(C)).

Figure 9:
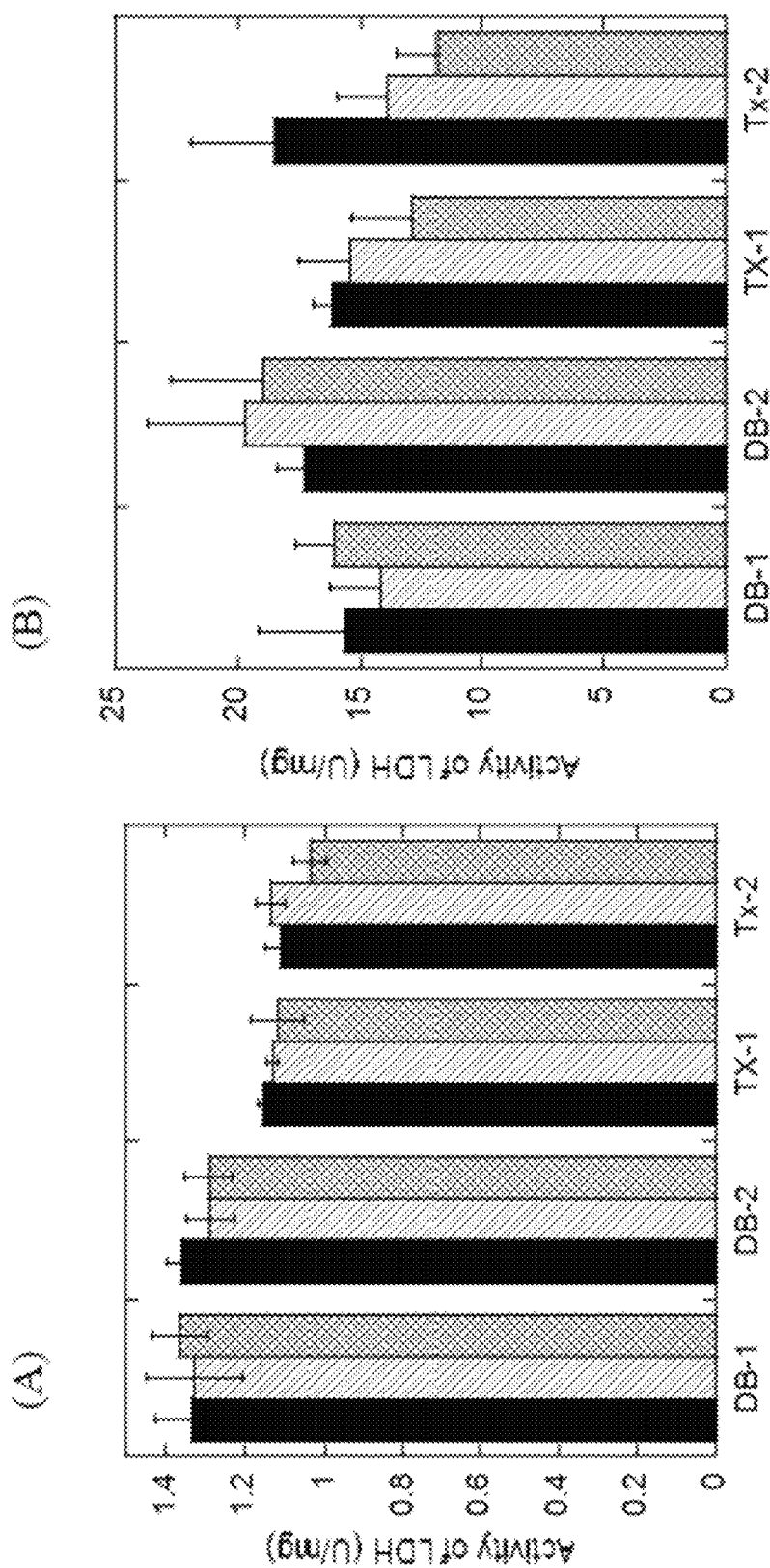
FIG. 9 illustrates the preserved activity of the intracellular enzyme lactate dehydrogenase (LDH) in proteins extracted using various reagents from (A) HUVECs and (B) HEK cells, at t=0 (solid bars), t=4 hours at 4° C. (diagonal bars), and t=4 hours at RT (cross-hatched bars).

FIG. 9 illustrates the preserved activity of LDH in proteins extracted using various reagents from (A) HEK cells and (B) HUVECs, at t=0 (solid bars), t=4 h at 4° C. (diagonal bars), and t=4 h at RT (cross-hatched bars). Significant amounts of LDH were detected in all samples (FIG. 9(B), HUVECs). DPS:B30-based and TX-based reagents yielded high amounts of LDH. However, unlike GAPDH, the amount of LDH did not decrease with time either at 4° C. or at RT (FIG. 9(B)). The sustained activity of LDH after 4 hours indicates the stability of LDH and resistance to proteolytic degradation. Similar observations were made for HEK cells (FIG. 9(A)).

Example 12: Role of Protease Inhibitor

Figure 10:
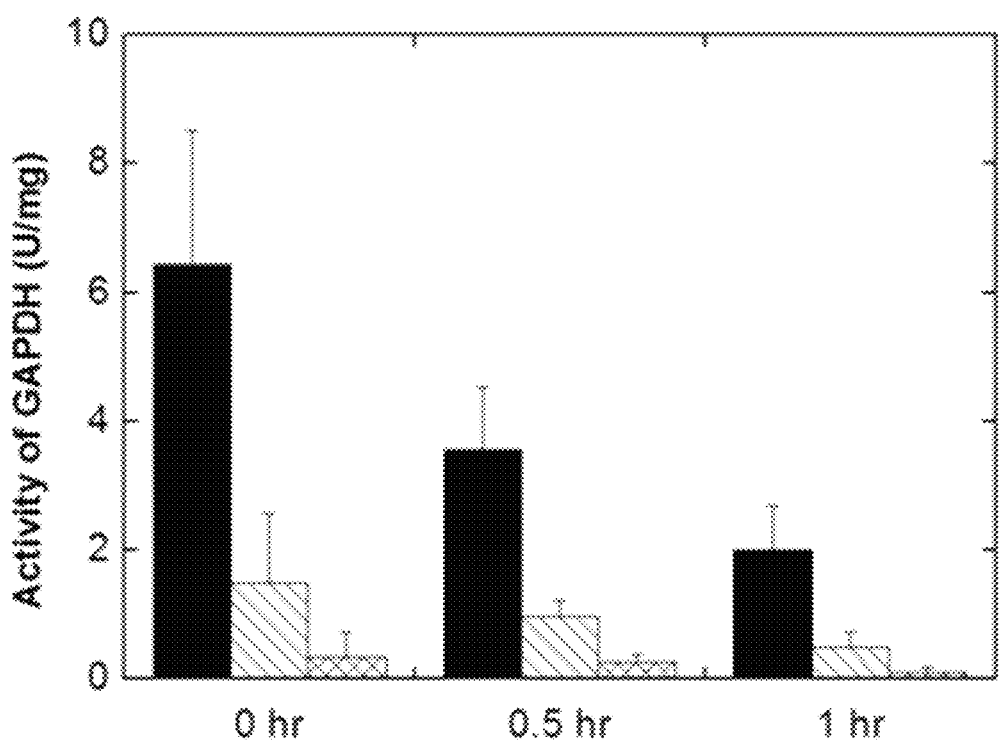
FIG. 10 illustrates the preserved activity of GAPDH in proteins extracted from HEK cells using a composition comprising 3-(decyl dimethyl ammonio) propane sulfonate, polyoxyethylene (4) lauryl ether, and a protease inhibitor (DB-2), at 4 (solid bars), 10 (diagonal bars) and 24 hours (cross-hatched bars).

The effect of a delay between cell solubilization and addition of protease inhibitor on preservation of enzyme activity was studied. FIG. 10 illustrates the preserved activity of GAPDH in proteins extracted from HEK cells using DB-2, at 4 h (solid bars), 10 h (diagonal bars) and 24 h (cross-hatched bars). When protease inhibitors were added at zero time (as is done in the normal preparation of DB-2), significant activity was preserved at the end of four hours (FIG. 10). The activity decreased with time; however, detectable activity was observed even after 24 hours post-solubilization (FIG. 10). A delay of 30 or 60 min between cell solubilization with DB-1 and addition of protease inhibitor produced an adverse effect on GAPDH activity. A 30 min delay reduced the activity of GAPDH at 4 hours by about 50%, and a 60 min delay reduced the activity by about 60% (FIG. 10) compared to that observed for no delay. Proportionate drops in GAPDH activity were seen at 10 h and 24 h. Collectively, the data suggest that the protease inhibitor provided the most pronounced benefit when added during cell solubilization.

Example 13: Tissue Solubilization

Brain, heart, liver, and skin tissues were collected from euthanized mice and stored at −80° C. until use. About 15 mg of each tissue was placed into a 2 ml tube and 400 µl of chilled lysis buffer was added to the tube. Tissue was homogenized using a homogenizer (IKA, NC, USA) at 13,000 rpm for 1 min.

Figure 11:
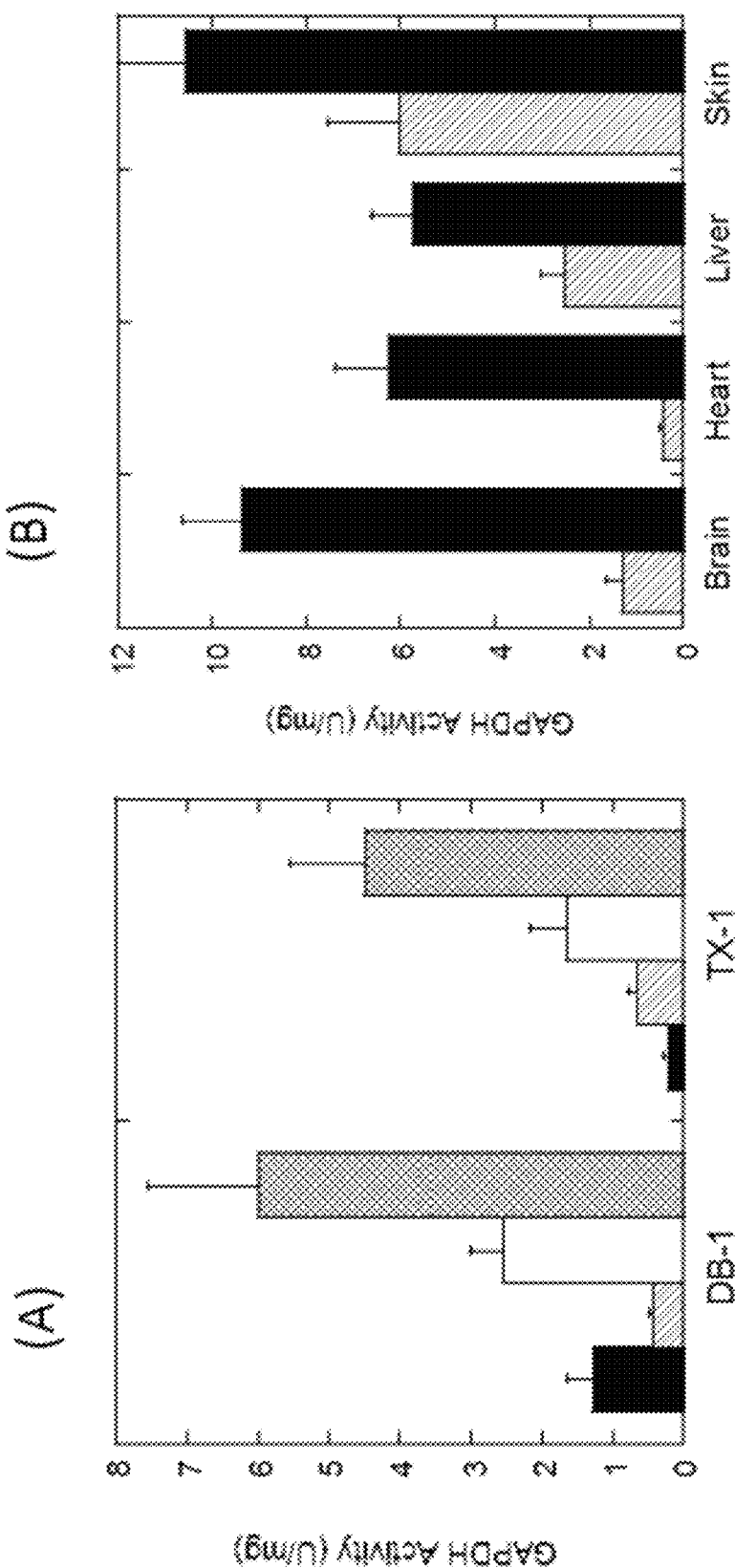
FIG. 11 illustrates (A) a comparison of the preserved activity of GAPDH in proteins extracted from various tissues (brain (solid bars), heart (diagonal bars), liver (open bars), and skin (cross-hatched bars)) using a composition comprising 3-(decyl dimethyl ammonio) propane sulfonate and polyoxyethylene (4) lauryl ether (DB-1) versus using Triton X-100 (TX-1), and (B) a comparison of the preserved activity of GAPDH in proteins extracted from the various tissues using DB-1 (diagonal bars) versus using DB-2 (solid bars).

DB-1 and TX-1 were used to dissolve brain, heart, liver, and skin tissue (FIG. 11). FIG. 11 illustrates (A) a comparison of the preserved activity of GAPDH in proteins extracted from the various tissues (brain (solid bars), heart (diagonal bars), liver (open bars), and skin (cross-hatched bars)) using DB-1 versus using TX-1; and (B) a comparison of the preserved activity of GAPDH in proteins extracted from the various tissues using DB-1 (diagonal bars) versus using DB-2 (solid bars). There was a significant difference in the GAPDH activity among the various tissues. The highest activity was found in the skin tissue and the least activity was found in the heart tissue. The impact of the protease inhibitor on the activity of GAPDH was studied by solubilizing the tissues in DB-2 and comparing to the tissues solubilized in DB-1. GAPDH activities in DB-2 were two to twelve times higher than those in DB-1.

Example 14: Protein Recovery from Skin

In an effort to understand signaling events in skin following UV exposure, we irradiated chemically-depilated wild-type C57BL/6 mice (10 kJ/m$^2$ of UVB; Oriel, solar simulator) and isolated protein at 1, 6, and 24 h post-irradiation by gently abrading skin in an ice cold buffer comprising DPS and B30 as well as TX-2 (0.25% w/v DPS and 0.25% v/v B30 in TX-2). The combination buffer was used because the proteins were analyzed using RPPA, which requires sodium dodecyl sulfate (SDS)-based denaturation of proteins, thus prioritizing tissue solubilization and lysis over preservation of activity. Hence, a combination of DPS:B30 and TX-2 was used for skin solubilization. Total protein recovered averaged approximately 500 to 1200 μg per cm$^2$ of epidermis. The recovered protein was subjected to RPPA for over 140 phosphoproteins and proteins involved in signaling, apoptosis, autophagy, and cell cycle regulation. Following unsupervised hierarchical clustering (Treeview), several functional groups were identified.

Figure 12:
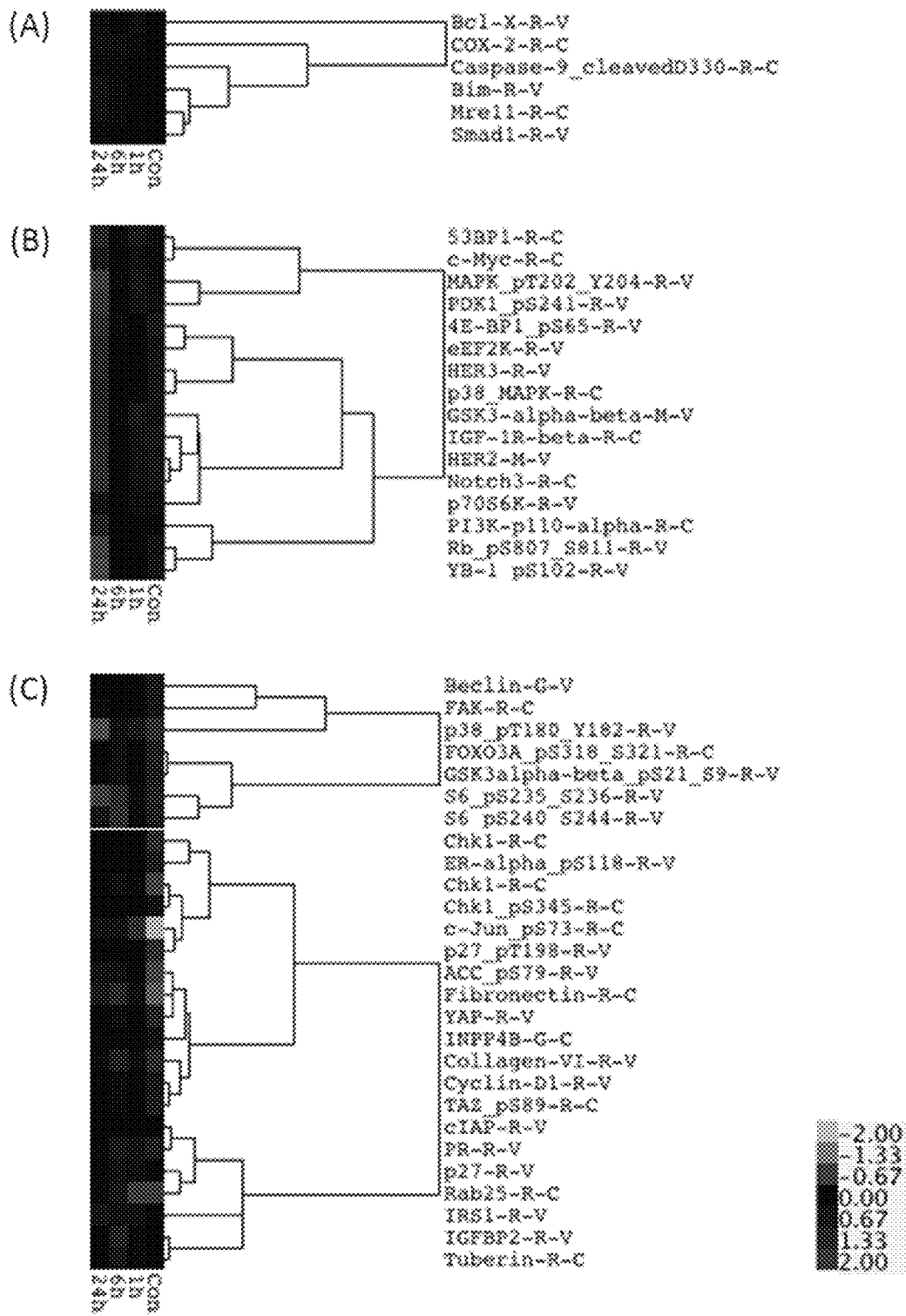
FIG. 12 illustrates phosphoproteins isolated from mouse epidermis that had been irradiated with 10 kJ/m$^2$ of UVB, solubilized with DB-1 in Triton X-100 containing a protease inhibitor (TX-2), and subjected to reverse phase protein array (RPPA).

FIG. 12 illustrates the solubilized, isolated phosphoproteins. A number of inflammatory and apoptotic effectors including Cox2, Bim, and Bcl-XL were slightly induced by 24 h (FIG. 12(A)). Many proteins associated with cell cycle progression, such as phospho-pRB (Rb_pS807) and phospho-ERK2 (MAPK_pT202_Y204), were down regulated by 24 h consistent with cell cycle arrest following irradiation (FIG. 12(B)). Finally, multiple stress activated responses were evident within hours, including the early up regulation of phospho-p38 (p38_pT180_Y182), Chk1 kinase, phospho S6 (pS235_S236; pS240_S244) and phospho-c-Jun (cJun_pS73) (FIG. 12(C)). The exquisite time dependence of these responses reinforces the complexity and specificity of multiple phosphoprotein signaling cascades in skin following UV exposure. Therefore, the ability to quickly solubilize tissues for this type of analysis is critically important.

Example 15: Characterization of Micelles

Hydrodynamic diameter and zeta potential of micelles were measured for B30, DPS, DB-1, and TX-1 using a Zetasizer Nano ZS instrument (Malvern). The mean size distribution was assessed by dynamic light scattering (DLS). Zeta potentials were measured by electrophoretic light scattering (ELS). The smallest hydrodynamic diameters of micelles were ranked in this order: DPS (4.952 nm)<TX1 (12.45 nm)<DB-1 (44.4 nm)<B30 (132.3 nm). Micelles of DB1, DPS and TX1 had a single peak in intensity size distribution with polydispersity index 0.186, 0.045, and 0.0875, respectively. On the other hand, micelles of B30 had several peaks. Zeta potentials of micelles were ranked in this order: DPS (−17.7 mV)>DB1 (−4.5 mV)>B30 (−3.8 mV)>TX1 (−2.0 mV). Table 1 lists several properties of each surfactant.

TABLE 1

Properties of each surfactant.

| | M.W. | CMC (mM) | Micelle diameter (nm) | Aggregation number | HLB | Zeta Potential (mV) |
|---|---|---|---|---|---|---|
| B30 | 362.54 | 0.02-0.04 | 110<br>132.2$^m$ | 90 | 9.7 | −3.8 |
| DPS | 307.49 | 39 | 4.95$^m$ | 41 | — | −17.7 |
| Triton-X100 | 625 | 0.24 | 8.6<br>12.45$^m$ | 140 | 13.5 | −2.0 |
| DB-1 | — | — | 44.4$^m$ | — | — | −4.5 |

$^m$ = measured in this study.

DPS possesses a negatively charged surface (zeta potential of −17.7 mV), which can deactivate protein activity. B30, on the other hand, is relatively inert. A combination of DPS and B30 offers an unexpected synergistic effect between the high potency of DPS with the inertness of B30. Indeed, the zeta potential of DB-1 (−4.5 mV) is significantly lower from that of DPS (−17.7 mV). B30 is a relatively hydrophobic surfactant and forms a cloudy suspension in PBS. Addition of DPS solubilizes B30 and may yield a transparent micellar solution with a particle diameter of 40.4 nm. The estimated critical micelle concentration of the DPS:B30 mixture may be 0.045-0.090 mM. This concentration is significantly lower than the concentration of DPS and B30 in DB-1 (7.45 and 6.54 mM, respectively). Accordingly, DB-1 is expected to exist in the micellar form.

Example 16: Antibacterial Activity of DPS:B30

Figure 13:
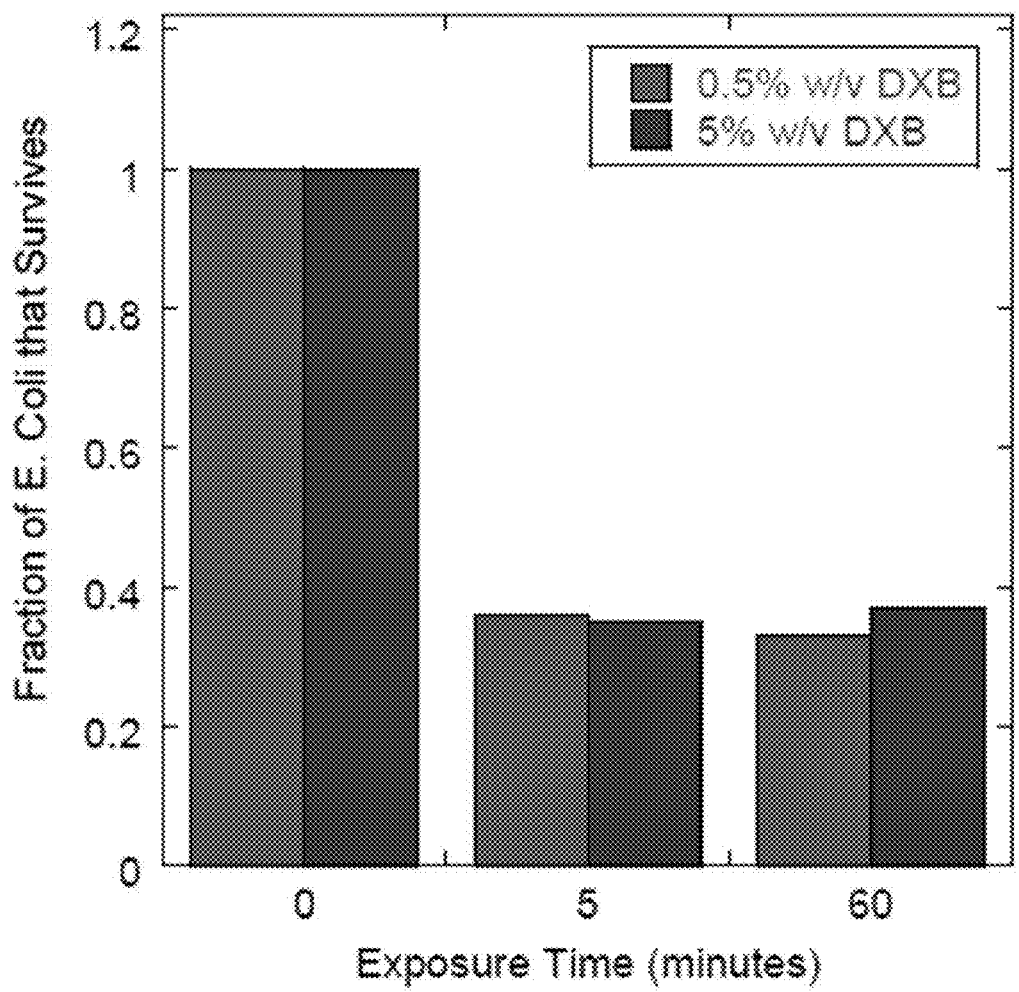
FIG. 13 illustrates the antibacterial activity versus E. Coli of two compositions comprising a 1:1 mixture of 3-(decyl dimethyl ammonio) propane sulfonate and polyoxyethylene (4) lauryl ether (0.5% w/v and 5.0% w/v).

Two compositions comprising a 1:1 mixture of DPS:B30 (0.5% w/v and 5.0% w/v) were tested for their antibacterial activity versus *E. Coli*. FIG. 13 illustrates the results.

The above Examples illustrate that the compositions described herein may provide at least three unexpected and surprising results: (1) a high fraction of solubilized proteins, including cytosolic proteins, from various cells and tissues; (2) protection of the proteins against denaturation and/or deactivation; and (3) significant antibacterial activity.

To the extent that the term "includes" or "including" is used in the specification or the claims, it is intended to be inclusive in a manner similar to the term "comprising" as that term is interpreted when employed as a transitional word in a claim. As used in the specification and the claims, the singular forms "a," "an," and "the" include the plural. Furthermore, to the extent that the term "or" is employed (e.g., A or B), it is intended to mean "A or B or both." When the applicants intend to indicate "only A or B but not both," then the term "only A or B but not both" will be employed. Thus, use of the term "or" herein is the inclusive, and not the exclusive use. See Bryan A. Gamer, A Dictionary of Modern Legal Usage 624 (2d. Ed. 1995). Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, with the benefit of the disclosure provided in this application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A method for solubilizing skin cells and/or skin tissue of a subject in vivo, the method comprising:
    contacting the skin cells and/or skin tissue of the subject in vivo with a buffered composition effective to solubilize the skin cells and/or skin tissue of the subject in vivo, the buffered composition comprising:
    a 3-(alkyl dimethyl ammonia) propane sulfonate zwitterionic surfactant; and
    a polyethylene glycol alkyl ether nonionic surfactant,
    the buffered composition being characterized by a pH of between about 7 and about 9,
    provided that the zwitterionic surfactant and the nonionic surfactant are not simultaneously and respectively 3-(decyl dimethyl ammonia) propane sulfonate and polyoxyethylene (4) lauryl ether.

2. The method of claim 1, further comprising subjecting the skin cells and/or skin tissue to energy.

3. The method of claim 1, further comprising collecting from the solubilized skin cells and/or skin tissue one or more of: a small organic molecule, a protein, DNA, RNA, and a lipid.

4. The method of claim 1, further comprising collecting at least one of cytosolic proteins, nuclear proteins, and surface proteins from the solubilized skin cells and/or skin tissue.

5. The method of claim 1, wherein the buffered composition further comprises a protease inhibitor.

6. The method of claim 1, wherein the skin cells comprise at least one of endothelial cells and keratinocyte cells.

7. The method of claim 1, the buffered composition comprising one or more of: phosphate-buffered saline, Tris-buffered saline, Tris-hydrochloride, and ethylene diamine tetraacetic acid.

8. The method of claim 1, wherein the composition further comprises a buffer solution, the pH of the composition in the buffer solution being about 8.8.

9. The method of claim 1, the buffered composition characterized by a total (w/v) concentration of the zwitterionic and nonionic surfactants of one or more of: between about 0.01% and about 10%; between about 0.01% and about 5%; between about 0.1% and about 2%; between about 0.1% and about 0.5%; and about 1%.

10. The method of claim 1, the buffered composition characterized by a concentration ratio of the zwitterionic surfactant to the nonionic surfactant of between about 2:3 and about 3:2.

11. A method for recovering proteins from skin cells of a subject in vivo, the method comprising:
    contacting the skin cells of the subject in vivo with a buffered composition effective to provide solubilized proteins from the skin cells of the subject in vivo, the buffered composition comprising:
    a 3-(alkyl dimethyl ammonia) propane sulfonate zwitterionic surfactant; and
    a polyethylene glycol alkyl ether nonionic surfactant, the buffered composition being characterized by a pH of between about 7 and about 9, provided that the zwitterionic surfactant and the nonionic surfactant are not simultaneously and respectively 3-(decyl dimethyl ammonia) propane sulfonate and polyoxyethylene (4) lauryl ether; and
    subjecting the solubilized proteins to a reverse phase protein array.

12. The method of claim 11, wherein the buffered composition further comprises an alkyl sulfate surfactant or a salt thereof.

13. The method of claim 11, wherein the solubilized proteins comprise signaling proteins.

14. The method of claim 11, further comprising performing unsupervised hierarchical clustering to identify the solubilized proteins.

15. The method of claim 11, the buffered composition characterized by a total (w/v) concentration of the zwitterionic and nonionic surfactants of one or more of: between about 0.01% and about 10%; between about 0.01% and about 5%; between about 0.1% and about 2%; between about 0.1% and about 0.5%; and about 1%.

16. The method of claim 11, the buffered composition characterized by a concentration ratio of the zwitterionic surfactant to the nonionic surfactant of between about 2:3 and about 3:2.

* * * * *